United States Patent [19]

Watson et al.

[11] Patent Number: 4,929,269
[45] Date of Patent: May 29, 1990

[54] HERBICIDAL SULFONOMIDES

[75] Inventors: Keith G. Watson, Blackburn; Peter Drygala, Niddrie; Stephen Bell, Vale, all of Australia

[73] Assignee: ICI Australia Operations Proprietary Limited, Melbourne, Australia

[21] Appl. No.: 259,762

[22] Filed: Oct. 19, 1988

[30] Foreign Application Priority Data

Oct. 20, 1987 [AU] Australia ................... PI4989

[51] Int. Cl.$^5$ .............. C07D 401/12; C07D 403/12; C07D 417/12; A01N 43/54

[52] U.S. Cl. ................................ 71/92; 71/90; 71/91; 544/52; 544/105; 544/295; 540/491; 540/504; 540/505; 540/518; 540/512; 540/513

[58] Field of Search ............... 71/90, 91, 92; 544/52, 544/105, 295; 540/491, 504, 505, 518, 512, 513

[56] References Cited

U.S. PATENT DOCUMENTS

| | | | |
|---|---|---|---|
| 4,586,950 | 5/1986 | Pasteris | 71/92 |
| 4,634,465 | 1/1987 | Ehrenfreund et al. | 71/91 |
| 4,677,212 | 6/1987 | Ehrenfreund et al. | 549/15 |
| 4,752,322 | 6/1988 | Dumas et al. | 71/92 |

*Primary Examiner*—John M. Ford
*Attorney, Agent, or Firm*—Cushman, Darby & Cushman

[57] ABSTRACT

Compounds of the formula

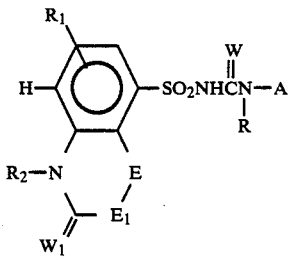

and salts thereof, W and W$_1$ being independently O and S, A being a nitrogen-containing heterocyclic ring system, E being O, S(O)m or NR$_3$ where m is 0–2, R$_1$, R$_2$ and R$_3$ is hydrogen, C$_1$–C$_4$ alkyl or C$_2$–C$_4$ alkenyl or alkynyl and E$_1$ being hydrogen, halogen or one of a variety of organic substituents.

The compounds are effective herbicides.

10 Claims, No Drawings

HERBICIDAL SULFONOMIDES

This invention relates to organic compounds having biological activity and in particular to organic compounds having herbicidal properties and plant growth regulating properties, to processes for the preparation of such compounds, to intermediates useful in the preparation of such compounds and to herbicidal compositions and processes utilizing such compounds.

The use of certain sulfonylurea derivatives as herbicides is known in the art. Thus, for example, the "Pesticide Manual" (C R Worthing Editor, The British Crop Protection Council, 7th Edition 1983) describes the sulfonylurea derivative known commercially as chlorsulfuron [1-(2-chlorophenylsulfonyl)-3-(4-methoxy-6-methyl-1,3,5-triazin-2-yl) urea] and its use as a broadleaf weed herbicide in cereals. This compound is described in Australian Patent No. 510,056 and its equivalents such as U.S. Pat. No. 4,127,405.

Australian Patent Application No. 89,354/82 (published April 21, 1983) discloses herbicidal benzenesulfonylureas including those of general formulae 1 and 2:

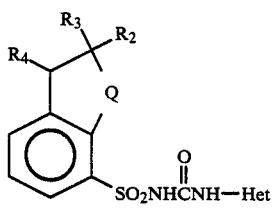

1

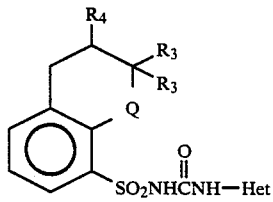

2 wherein
Q is O, S or $SO_2$;
$R_2$ is H or $C_1$ to $C_3$ alkyl;
$R_3$ and $R_4$ are H or $CH_3$;
Het is a pyrimidyl or triazinyl heterocyclic ring.

European Patent Application 82,681 (published June 29, 1983) discloses herbicidal benzene-sulfonylureas including those of general formulae 3 and 4:

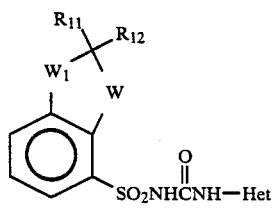

3

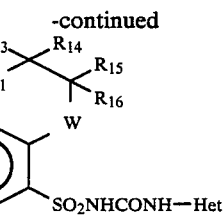

4

Wherein:
W and $W_1$ are O, S, SO or $SO_2$;
$R_{11}$ is H or $CH_3$;
$R_{12}$ is H or $C_1$ to $C_4$ alkyl;
$R_{13}$, $R_{14}$, $R_{15}$ and $R_{16}$ are independently H or $CH_3$;
Het is a pyrimidyl or triazinyl heterocyclic ring.

Australian Patent Application No. 20659/83 (published May 3, 1984) discloses herbicidal sulfonyl ureas including those of general formulae 5 and 6:

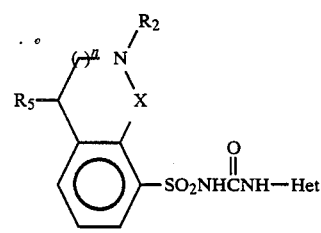

5

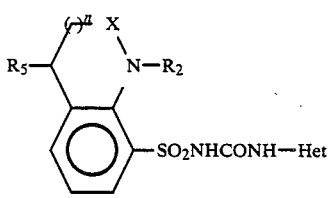

6 wherein
X is C=O or $SO_2$;
$R_2$ is H or $C_1$ to $C_4$ alkyl;
$R_5$ is H or $CH_3$;
n is 0, 1 or 2.

Australian Patent Application No. 16889/83 (published January 19, 1984) discloses herbicidal sulfonylureas of the general structure 7:

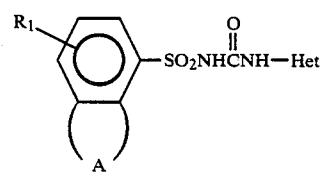

7 wherein
A is an unsubstituted or substituted bridge of 3 or 4 atoms which contains 1 or 2 oxygen, sulfur or nitrogen atoms and, together with the linking carbon atom, forms a non-aromatic 5- or 6-membered heterocyclic ring system, with the proviso that two oxygen atoms are separated by at least one carbon atom and that oxygen and sulfur atoms are only linked to each other if the sulfur atom takes the form of the —SO— or $SO_2$— group;
$R_1$ is hydrogen, halogen, $NO_2$, $C_1$–$C_4$ alkyl, $C_1$–$C_4$ haloalkyl, $C_1$–$C_4$ alkoxy, $C_1$–$C_4$ haloalkoxy, $C_1$–$C_4$ alkoxycarbonyl, $C_1$–$C_4$ alkylthio, $C_1$–$C_4$ alkylsulfinyl, $C_1$–$C_4$ alkylsulfonyl or $C_2$–$C_5$ alkoxyalkoxy; Het is a pyrimidyl or triazinyl heterocyclic ring.

Australian Patent Application No. 54,625/86 (published October 16, 1986) discloses herbicidal sulfonylureas including those of the general structure 8:

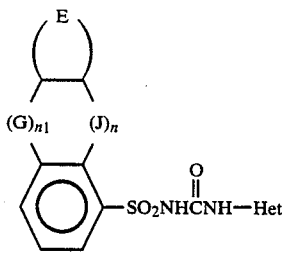

wherein

G is $CH_2$, $CH_2CH_2$, O, S, NH, $NCH_3$ or $CH=CH$;

J is $CH_2$, $C=O$, $S(O)_m$, O, NH, $NCH_3$, CHOH, $CHOCH_3$, $CH(CH_3)$ or $C(CH_3)OH$; n and $n_1$ are independently 0 or 1, m is 0, 1 or 2; E is a bridge of 3 or 4 atoms containing 0 to 2 heteroatoms; Het is a pyrimidyl or triazinyl heterocyclic ring.

SUMMARY OF THE INVENTION

It has now been found that a new group of bicyclic sulfonylurea derivatives exhibit particularly useful herbicidal activity.

Accordingly the invention provides a compound of the formula I

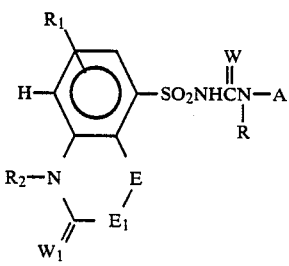

wherein

W and $W_1$ are independently O or S;

E is O, $S(O)_m$, or $N-R_3$;

$E_1$ is $CH_2$, $CH_2CH_2$, $CH(C_1$–$C_4$ alkyl), $C(CH_3)_2$ or CH aryl; $R_1$ hydrogen, halogen, $C_1$–$C_4$ alkyl, $C_1$–$C_4$ haloalkyl, nitro, $C_1$–$C_4$ alkoxy, $C_1$–$C_4$ haloalkoxy, cyano, $C_1$–$C_4$ alkoxycarbonyl, $C_1$–$C_4$ alkylthio, $C_1$–$C_4$ alkylsulfinyl, $C_1$–$C_4$ alkylsulfonyl, sulfamoyl, $C_1$–$C_4$ alkylsulfamoyl, di($C_1$–$C_4$ alkyl) sulfamoyl, amino, $C_1$–$C_4$ alkylamino or di($C_1$–$C_4$ alkyl) amino;

R, $R_2$ and $R_3$ are each independently hydrogen, $C_1$–$C_4$ alkyl, $C_2$–$C_4$ alkenyl, or $C_2$–$C_4$ alkynyl;

m = 0, 1 or 2

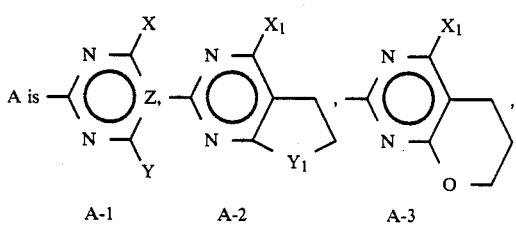

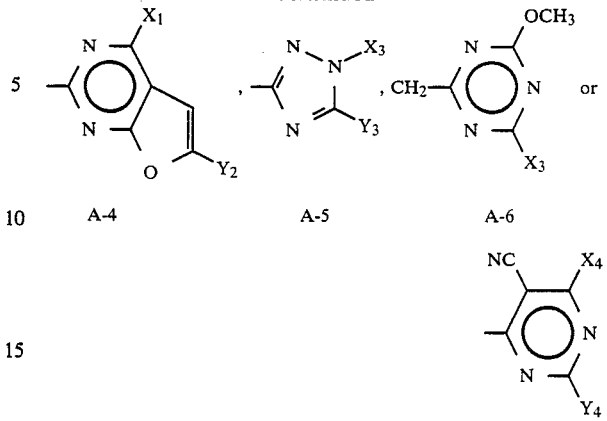

X is $CH_3$, $OCH_3$, $OCH_2CH_3$, Cl, F, Br, I, $OCF_2H$, $CH_2F$ or $CF_3$,

Y is H, $CH_3$, $OCH_3$, $OC_2H_5$, $CH_2OCH_3$, $NH_2$, $NHCH_3$, $N(CH_3)_2$, $C_2H_5$, $CF_3$, $SCH_3$, $N(OCH_3)CH_3$, $OCH_2CH=CH_2$, $OCH_2C\equiv CH$, $OCH_2CF_3$, cyclopropyl, $OCH_2CH_2OCH_3$, $CH_2SCH_3$, $(C=O)R_4$, $CR_4(QCH_3)_2$,

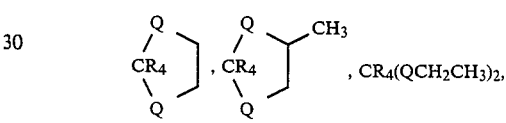

$OCF_2H$, $SCF_2H$, $C\equiv CH$ or $C\equiv CCH_3$, where Q is O or S and $R_4$ is H or $CH_3$;

Z is CH, N, $CCH_3$, $CC_2H_5$, CCl or CBr;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $C_2H_5$ or $CH_2CF_3$;

$Y_3$ is $OCH_3$, $OC_2H_5$, $SCH_3$, $SC_2H_5$, $CH_3$ or $CH_2CH_3$;

$X_3$ is $CH_3$ or $OCH_3$;

$Y_4$ is $CH_3$, $OCH_3$, $OCH_2CH_3$ or Cl; and $X_4$ is $CH_3$, $OCH_3$, $OCH_2CH_3$, $CH_2OCH_3$ or Cl.

The invention also comprises the salts which the compounds of formula 1 are able to form with amines, alkali metal bases and alkaline earth metal bases, or with quaternary ammonium bases.

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butyl isomers.

Alkenyl denotes straight chain or branched alkenes, e.g., vinyl, 1-propenyl, 2-propenyl, 3-propenyl or the different butenyl isomers.

Alkylsulfonyl denotes methylsulfonyl, ethylsulfonyl or the different propylsulfonyl isomers.

Alkylthio, alkylsulfinyl, alkylamino, etc. are defined in an analogous manner.

Preferred values of E, are $CH_2$, $CH_2CH_2$, $CH(C_1$–$C_4$ alkyl) and $C(CH_3)_2$.

Preferred compounds of the invention include:

(1) Those compounds of formula I where W is O and A is A-1.

(2) Compounds of Preferred (1) where
R is hydrogen;
$R_1$ is hydrogen, fluorine, chlorine, bromine, methyl, methoxy, trifluoromethyl or methylthio; and
Y is methyl, methoxy, ethoxy, methoxymethyl, trifluoromethyl, 2,2,2-trifluoroethoxy, dimethoxymethyl or difluoromethoxy.

A further group of preferred compounds of formula I comprises those compounds wherein:
E is O, S, NH or $NCH_3$;
$E_1$ is $CH_2$, $CH_2CH_2$, or $CH(CH_3)$;
$W_1$ is O, and $R_2$ is hydrogen, methyl or ethyl.

Examples of the basic types of condensed saturated heterocyclic systems which are attached to the sulfonyl end of the sulfonylurea bridge are:
3-oxo-3,4-dihydro-2H-1,4-benzoxazines $B_1$,
3-oxo-3,4-dihydro-2H-1,4-benzothiazines $B_2$,
2-oxo-1,2,3,4-tetrahydroquinoxalines $B_3$,
2,3-dihydro-1,5-benzoxazepin-4-ones $B_4$,
2,3-dihydro-1,5-benzothiazepin-4-ones $B_5$, and
3,4-dihydro-1,5-benzodiazepine-2-ones $B_6$.

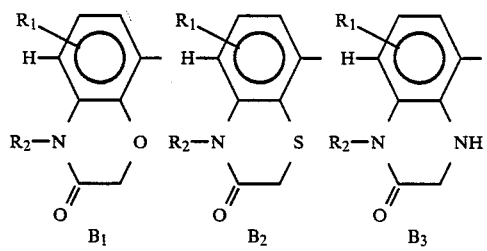

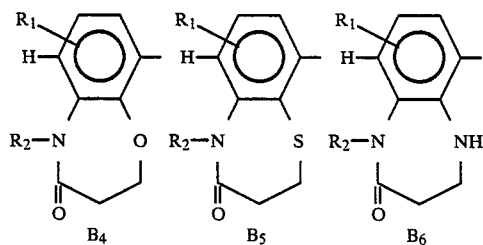

Specific examples of the compounds of the invention include those compounds listed in Tables Ia–Ig.

TABLE 1a

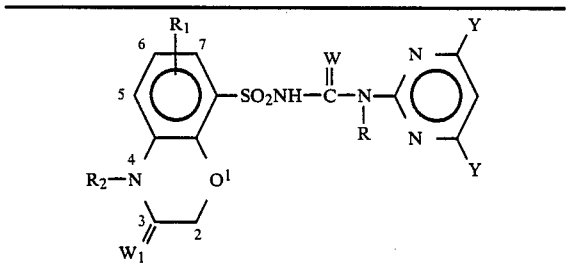

| Compound No. | $R_1$ | $R_2$ | $W_1$ | W | R | X | Y |
|---|---|---|---|---|---|---|---|
| 1 | H | H | O | O | H | Me | Me |
| 2 | H | H | O | O | H | Me | OMe |
| 3 | H | H | O | O | H | OMe | OMe |
| 4 | H | H | O | O | H | Cl | OMe |
| 5 | H | H | O | O | H | Me | OEt |
| 6 | H | H | O | O | H | Cl | NHMe |
| 7 | H | H | O | O | H | $OCF_2H$ | $OCF_2H$ |
| 8 | H | H | O | O | H | Cl | $NMe_2$ |
| 9 | H | H | O | O | H | Cl | $NH_2$ |

TABLE 1a-continued

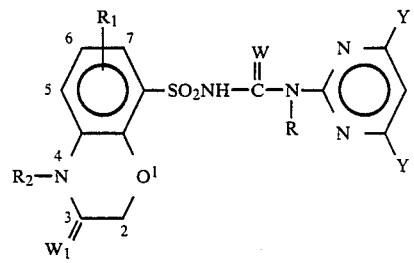

| Compound No. | $R_1$ | $R_2$ | $W_1$ | W | R | X | Y |
|---|---|---|---|---|---|---|---|
| 10 | H | H | O | O | H | Me | SMe |
| 11 | H | H | O | O | H | Me | $CH_2OMe$ |
| 12 | H | H | O | O | H | $CF_3$ | OMe |
| 13 | H | H | O | O | H | OMe | $OCF_2H$ |
| 14 | H | H | O | O | H | OMe | $NMe_2$ |
| 15 | H | H | O | O | Me | Me | OMe |
| 16 | H | H | O | O | Me | OMe | OMe |
| 17 | H | H | O | O | H | Me | OMe |
| 18 | H | H | O | O | H | OMe | OMe |
| 19 | H | H | S | O | H | OMe | OMe |
| 20 | H | H | S | O | H | Me | OMe |
| 21 | H | H | S | O | H | $OCF_2H$ | $OCF_2H$ |
| 22 | H | H | S | O | H | Cl | OMe |
| 23 | H | Et | O | O | H | OMe | OMe |
| 24 | H | Allyl | O | O | H | OMe | OMe |
| 25 | H | Me | O | O | H | Me | OMe |
| 26 | H | Me | O | O | H | OMe | OMe |
| 27 | H | Me | S | O | H | Me | OMe |
| 28 | H | Me | S | O | H | OMe | OMe |
| 29 | H | Me | O | O | H | Cl | OMe |
| 30 | H | Me | O | O | H | $OCF_2H$ | $OCF_2H$ |
| 31 | 6-F | H | O | O | H | Me | OMe |
| 32 | 6-F | H | O | O | H | OMe | OMe |
| 33 | 6-F | H | O | O | H | $OCF_2H$ | $OCF_2H$ |
| 34 | 6-F | H | O | O | Me | OMe | OMe |
| 35 | 6-F | H | S | O | H | OMe | OMe |
| 36 | 6-F | Me | O | O | H | OMe | OMe |
| 37 | 6-F | Me | O | O | H | Me | OMe |
| 38 | 6-Cl | H | O | O | H | Me | OMe |
| 39 | 6-Cl | H | O | O | H | OMe | OMe |
| 40 | 6-Cl | H | S | O | H | Cl | OMe |
| 41 | 6-Cl | H | O | O | H | Cl | OMe |
| 42 | 6-$CF_3$ | H | O | O | H | Me | OMe |
| 43 | 6-$CF_3$ | H | O | O | H | OMe | OMe |
| 44 | 6-$NO_2$ | H | O | O | H | OMe | OMe |
| 45 | 6-$CH_3$ | H | O | O | H | Me | OMe |
| 46 | 6-$CH_3$ | H | O | O | H | OMe | OMe |
| 47 | 6-OMe | H | O | O | H | OMe | OMe |
| 48 | 6-OMe | H | O | O | H | Me | OMe |
| 49 | 6-$C(CH_3)_3$ | H | O | O | H | Me | OMe |
| 50 | 7-Cl | H | O | O | H | Me | OMe |
| 51 | 7-Cl | H | O | O | H | OMe | OMe |
| 52 | 7-OMe | H | O | O | H | Me | OMe |
| 53 | 7-OMe | H | O | O | H | OMe | OMe |
| 54 | 7-SMe | H | O | O | H | Me | OMe |
| 55 | 7-SMe | H | O | O | H | OMe | OMe |
| 56 | 6,7-$Cl_2$ | H | O | O | H | OMe | OMe |
| 57 | 6,7-$Me_2$ | H | O | O | H | OMe | OMe |
| 58 | 6,7-$(OMe)_2$ | H | O | O | H | OMe | OMe |
| 59 | 6-Cl,7-OMe | H | O | O | H | Me | OMe |
| 60 | 6-Cl,7-OMe | H | O | O | H | OMe | OMe |
| 61 | 7-$CO_2Me$ | H | O | O | H | Me | OMe |
| 62 | 7-$CO_2Me$ | H | O | O | H | OMe | OMe |
| 63 | 7-$NO_2$ | H | O | O | H | OMe | OMe |
| 64 | 7-$NO_2$ | Me | O | O | H | Me | OMe |

TABLE 1b

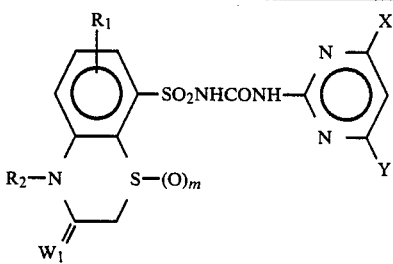

| Compound No. | R₁ | R₂ | W₁ | m | X | Y |
|---|---|---|---|---|---|---|
| 65 | H | H | O | 0 | Me | OMe |
| 66 | H | H | O | 0 | OMe | OMe |
| 67 | H | H | O | 0 | Me | Me |
| 68 | H | H | O | 0 | Cl | OMe |
| 69 | H | H | O | 0 | OCF₂H | OCF₂H |
| 70 | H | H | O | 0 | OMe | SMe |
| 71 | H | H | O | 0 | OMe | NMe₂ |
| 72 | H | H | S | 0 | Me | OMe |
| 73 | H | H | S | 0 | OMe | OMe |
| 74 | H | Me | O | 0 | Me | OMe |
| 75 | H | Me | O | 0 | OMe | OMe |
| 76 | H | Et | O | 0 | OMe | OMe |
| 77 | H | Allyl | O | 0 | OMe | OMe |
| 78 | 6-Cl | H | O | 0 | Me | OMe |
| 79 | 6-CF₃ | H | O | 0 | Me | OMe |
| 80 | 6-Cl | Me | O | 0 | Me | OMe |
| 81 | 6-F | Me | O | 0 | OMe | OMe |
| 82 | 7-Cl | H | O | 0 | OMe | OMe |
| 83 | 7-OMe | H | O | 0 | OMe | OMe |
| 84 | H | H | O | 1 | Me | OMe |
| 85 | H | H | O | 1 | OMe | OMe |
| 86 | H | H | O | 1 | Me | Me |
| 87 | H | H | O | 1 | Cl | OMe |
| 88 | H | H | O | 1 | OCF₂H | OCF₂H |
| 89 | H | H | S | 1 | OMe | OMe |
| 90 | H | H | S | 1 | Me | OMe |
| 91 | H | Me | O | 1 | Me | OMe |
| 92 | H | Me | O | 1 | OMe | OMe |
| 93 | H | Me | S | 1 | OMe | OMe |
| 94 | 6-Cl | H | O | 1 | Me | OMe |
| 95 | 6-Cl | H | O | 1 | OMe | OMe |
| 96 | 6-CH₃ | H | O | 1 | OMe | OMe |
| 97 | 7-Cl | H | O | 1 | OMe | OMe |
| 98 | H | H | O | 2 | Me | OMe |
| 99 | H | H | O | 2 | OMe | OMe |
| 100 | H | H | O | 2 | Me | Me |
| 101 | H | H | O | 2 | Cl | OMe |
| 102 | H | H | O | 2 | OCF₂H | OCF₂H |
| 103 | H | H | O | 2 | OMe | NMe₂ |
| 104 | H | H | O | 2 | OMe | NHMe |
| 105 | H | H | O | 2 | OMe | SMe |
| 106 | H | H | S | 2 | Me | OMe |
| 107 | H | H | S | 2 | OMe | OMe |
| 108 | H | Me | O | 2 | OMe | OMe |
| 109 | H | Me | O | 2 | Me | OMe |
| 110 | 6-Cl | H | O | 2 | OMe | OMe |
| 111 | 6-CF₃ | H | O | 2 | OMe | OMe |
| 112 | 7-OMe | H | O | 2 | Me | OMe |
| 113 | 6-Cl | H | O | 1 | Me | Me |
| 114 | 6-Cl | H | O | 0 | Me | Me |

TABLE 1c

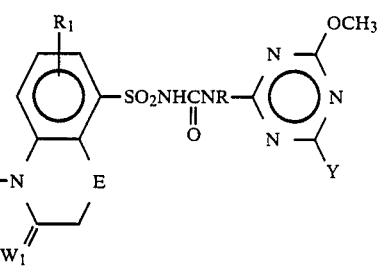

| Compound No. | R₁ | R₂ | W₁ | E | R | Y |
|---|---|---|---|---|---|---|
| 115 | H | H | O | O | H | Me |
| 116 | H | H | O | O | H | OMe |
| 117 | H | H | O | O | H | NMe₂ |
| 118 | H | H | O | O | H | SMe |
| 119 | H | H | O | O | H | OEt |
| 120 | H | H | O | S | H | Me |
| 121 | H | H | O | S | H | OMe |
| 122 | H | H | O | O | Me | Me |
| 123 | H | H | O | S | Me | Me |
| 124 | H | H | O | SO | H | Me |
| 125 | H | H | O | SO | H | OMe |
| 126 | H | H | O | SO₂ | H | Me |
| 127 | H | H | O | SO₂ | H | OMe |
| 128 | H | H | O | NH | H | Me |
| 129 | H | H | O | NH | H | OMe |
| 130 | H | H | O | NMe | H | OMe |
| 131 | H | H | O | NMe | H | Me |
| 132 | H | H | S | O | H | Me |
| 133 | H | H | S | O | H | OMe |
| 134 | H | H | S | S | H | Me |
| 135 | H | H | S | S | H | OMe |
| 136 | H | H | S | SO₂ | H | Me |
| 137 | H | H | S | SO₂ | H | OMe |
| 138 | H | H | S | NMe | H | Me |
| 139 | H | Allyl | O | O | H | Me |
| 140 | H | Me | O | O | H | Me |
| 141 | H | Me | O | O | H | OMe |
| 142 | H | Me | O | S | H | Me |
| 143 | H | Me | O | SO₂ | H | OMe |
| 144 | H | Et | S | O | H | Me |
| 145 | H | nPr | O | O | H | Me |
| 146 | H | Me | O | NMe | H | Me |
| 147 | 6-Cl | H | O | O | H | Me |
| 148 | 6-Cl | H | O | S | H | Me |
| 149 | 6-F | Me | O | O | H | OMe |

TABLE 1d

Structure: R₁-substituted benzene with SO₂NHCONH linked to pyrimidine (with X, Y substituents); benzene also bears R₂-N-C(=W₁) group with E/E₁ substituents.

| Compound No. | R₁ | R₂ | W₁ | E₁ | E | X | Y |
|---|---|---|---|---|---|---|---|
| 150 | H | H | O | CHMe | O | Me | OMe |
| 151 | H | H | O | CHMe | O | OMe | OMe |
| 152 | H | H | O | CHMe | O | Cl | OMe |
| 153 | H | H | O | CHMe | O | OCF₂H | OCF₂H |
| 154 | H | H | O | CHMe | S | Me | OMe |
| 155 | H | H | O | CHMe | S | OMe | OMe |
| 156 | H | H | O | CHMe | SO | Me | OMe |
| 157 | H | H | O | CHMe | SO₂ | OMe | OMe |
| 158 | H | H | O | CHMe | NMe | Me | OMe |
| 159 | H | H | O | CMe₂ | O | Me | OMe |
| 160 | H | H | O | CMe₂ | O | OMe | OMe |
| 161 | H | H | O | CMe₂ | SO₂ | OMe | OMe |
| 162 | H | H | O | CH | O | Me | OMe |
| 163 | H | H | O | CHnBu | O | OMe | OMe |
| 164 | H | H | O | CHEt | SO₂ | OMe | OMe |
| 165 | H | H | O | CHEt | SO₂ | Me | OMe |
| 166 | H | H | O | CHnBu | S | OMe | OMe |
| 167 | H | H | O | CHEt | S | OMe | OMe |
| 168 | H | H | S | CHMe | O | OMe | OMe |
| 169 | H | H | S | CHMe | O | Me | OMe |
| 170 | H | H | S | CHnBu | O | OMe | OMe |
| 171 | H | H | S | CHMe | S | OMe | OMe |
| 172 | H | Me | O | CHMe | O | Me | OMe |
| 173 | H | Me | O | CHMe | O | OMe | OMe |
| 174 | H | Me | S | CHMe | O | Me | OMe |
| 175 | H | Me | O | CHMe | S | Me | OMe |
| 176 | H | Et | O | CHMe | S | OMe | OMe |
| 177 | H | Allyl | O | CHMe | O | OMe | Me |
| 178 | H | Me | O | CHMe | SO | Me | OMe |
| 179 | H | Me | O | CHMe | SO₂ | Me | OMe |
| 180 | H | Me | O | CHMe | SO₂ | OMe | OMe |
| 181 | 6-F | H | O | CHMe | O | Me | OMe |
| 182 | 6-F | H | O | CHMe | O | OMe | OMe |
| 183 | 6-F | H | O | CHMe | O | Cl | OMe |
| 184 | 6-F | H | O | CHEt | O | OMe | OMe |
| 185 | 6-F | H | O | CHnPr | O | OMe | OMe |
| 186 | 6-F | H | O | CHnBu | O | OMe | OMe |
| 187 | 6-F | H | O | CMe₂ | O | OMe | OMe |
| 188 | H | Me | O | CMe₂ | O | Me | OMe |
| 189 | 6-F | H | O | CHMe | S | OMe | OMe |
| 190 | 6-F | H | O | CHMe | SO₂ | OMe | OMe |
| 191 | 6-F | H | S | CHMe | O | OMe | OMe |
| 192 | 6-F | Me | O | CHMe | O | OMe | OMe |
| 193 | 6-F | Me | O | CHMe | O | Me | OMe |
| 194 | 6-F | Me | O | CHnBu | O | OMe | OMe |
| 195 | 6-F | Me | O | CHMe | S | OMe | OMe |
| 196 | 6-F | Me | O | CHMe | SO₂ | OMe | OMe |
| 197 | 6-F | Me | O | CHMe | SO | OMe | OMe |
| 198 | 6-F | Me | S | CHMe | O | OMe | OMe |
| 199 | 6-F | Et | O | CHMe | O | OMe | OMe |
| 200 | 6-Cl | H | O | CHMe | O | OMe | OMe |
| 201 | 6-Cl | H | O | CHMe | S | Me | OMe |
| 202 | 6-Cl | H | O | CHMe | SO | Me | OMe |
| 203 | 6-Cl | H | O | CHMe | SO | Me | Me |
| 204 | 6-Cl | Me | O | CHMe | O | OMe | OMe |
| 205 | 6-Cl | Me | O | CHMe | S | Me | OMe |
| 206 | 6-Cl | Me | O | CHMe | SO₂ | OMe | OMe |
| 207 | 6-CF₃ | H | O | CHMe | S | Me | OMe |
| 208 | 6-CF₃ | H | S | CHMe | S | Me | OMe |
| 209 | 6-OMe | H | O | CHMe | O | OMe | OMe |
| 210 | 7-Cl | Me | O | CHMe | O | OMe | OMe |
| 211 | 7-OMe | Me | O | CHMe | O | OMe | OMe |
| 212 | 7-OMe | H | O | CHMe | O | Me | OMe |
| 213 | 7-OMe | H | O | CHMe | S | Me | OMe |
| 214 | 7-NO₂ | H | O | CHMe | O | OMe | OMe |

TABLE Ie

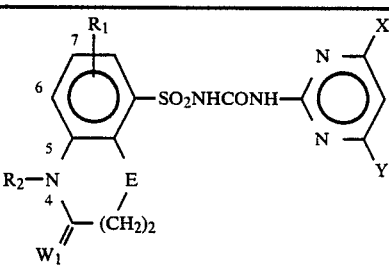

| Compound No. | R₁ | R₂ | W₁ | E | X | Y |
|---|---|---|---|---|---|---|
| 215 | H | H | O | O | OMe | OMe |
| 216 | H | H | O | O | Me | OMe |
| 217 | H | H | O | S | OMe | OMe |
| 218 | H | H | O | S | Me | OMe |
| 219 | H | H | S | O | OMe | OMe |
| 220 | H | Me | O | O | OMe | OMe |
| 221 | 7-F | H | O | O | OMe | OMe |
| 222 | 7-F | Me | O | O | OMe | OMe |
| 223 | 7-F | Me | O | SO₂ | OMe | OMe |
| 224 | H | H | O | NH | OMe | OMe |
| 225 | H | H | O | NMe | OMe | OMe |
| 226 | 7-CF₃ | H | O | S | Me | OMe |
| 227 | 7-CF₃ | Me | O | S | Me | OMe |
| 228 | 8-OMe | H | O | O | Me | OMe |
| 229 | 8-OMe | H | O | O | OMe | OMe |

TABLE If

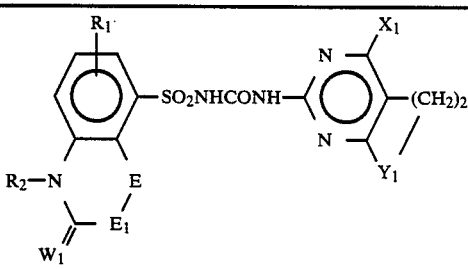

| Compound No. | R₁ | R₂ | W₁ | E₁ | E | X₁ | Y₁ |
|---|---|---|---|---|---|---|---|
| 230 | H | H | O | CH₂ | O | Me | CH₂ |
| 231 | H | H | O | CH₂ | O | OMe | CH₂ |
| 232 | H | H | O | CH₂ | O | OMe | O |
| 233 | H | H | O | CH₂ | S | OMe | O |
| 234 | H | H | O | CH₂ | SO₂ | OMe | CH₂ |
| 235 | H | H | O | CHMe | O | Me | O |
| 236 | H | H | S | CH₂ | O | Me | CH₂ |
| 237 | H | Me | O | CH₂ | O | Me | O |
| 238 | 6-F | Me | O | CHMe | O | OMe | CH₂ |
| 239 | 6,7-Me₂ | H | O | CH₂ | O | Me | CH₂ |

TABLE Ig

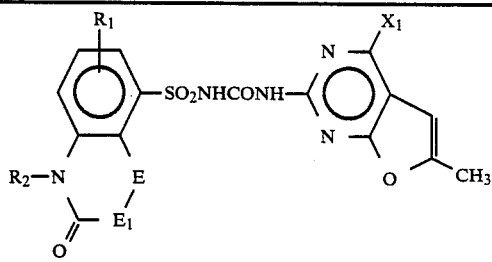

| Compound No. | R₁ | R₂ | E₁ | E | X₁ |
|---|---|---|---|---|---|
| 240 | H | H | CH₂ | O | Me |
| 241 | H | H | CH₂ | O | OMe |
| 242 | H | H | CH₂ | S | OMe |
| 243 | H | H | CH₂ | SO₂ | OMe |
| 244 | 6-F | Me | CHMe | O | Me |

TABLE Ig-continued

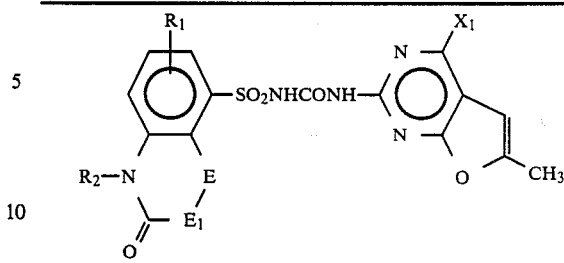

| Compound No. | R₁ | R₂ | E₁ | E | X₁ |
|---|---|---|---|---|---|
| 245 | 6-F | Me | CHMe | O | OMe |

TABLE Ih

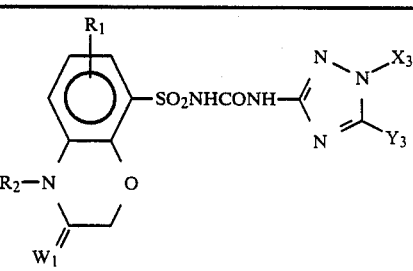

| Compound No. | R₁ | R₂ | W₁ | X₃ | Y₃ |
|---|---|---|---|---|---|
| 246 | H | H | O | Me | OMe |
| 247 | H | Me | O | Me | SMe |
| 248 | 6-F | Me | O | Me | OMe |
| 249 | H | Me | S | Et | OMe |

The compounds of the invention may be prepared by a variety of methods and in a further aspect the invention provides methods for the preparation of compounds of formula I.

Conveniently the preparation of the compounds of the invention can be considered in three parts.

Part A involves the preparation of fused phenylsulfonamides of the formula II

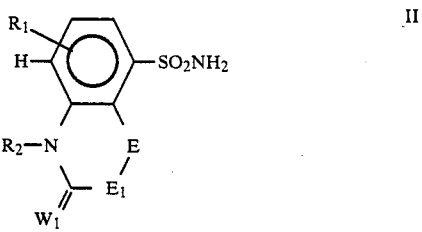

wherein $R_1$, $R_2$, $W_1$, E and $E_1$ are as defined for formula I. The sulfonamides of formula II can be prepared in a variety of ways including the general methods outlined below.

(a) The preparation of aromatic sulfonamides from the corresponding anilines by diazotization and reaction of the diazonium salt with sulfur dioxide is well known in the art (J. Org. Chem;, 25, 1824 (1960)).

Some of the necessary amino-benzo-azinones III have been described in the literature (see for example Rodds Chemistry of carbon compounds, Vol. IV H, p 463, 1978) and they may be prepared for example by reduction of the corresponding nitro compounds.

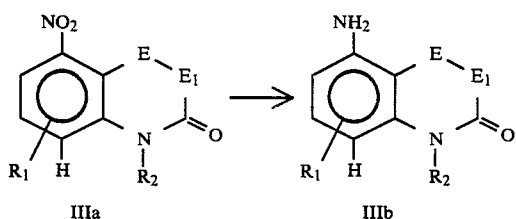

Alternatively the amino compounds IIIb (R₂=H) may be prepared by cyclization of certain 1,3-diamino benzenes IV which in turn are generally

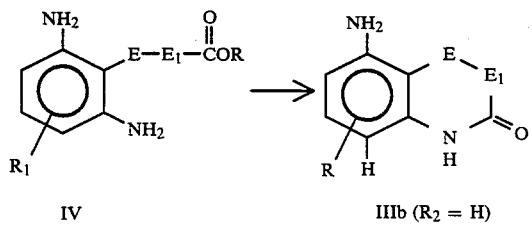

accessible from the corresponding dinitro benzenes V.

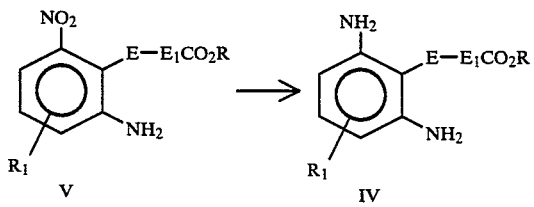

(b) The bicyclic aromatic sulfonamides II may also be prepared from suitable 3-nitro benezene sulfonamides VI which have a leaving group X (preferably halogen) at the 2 position.

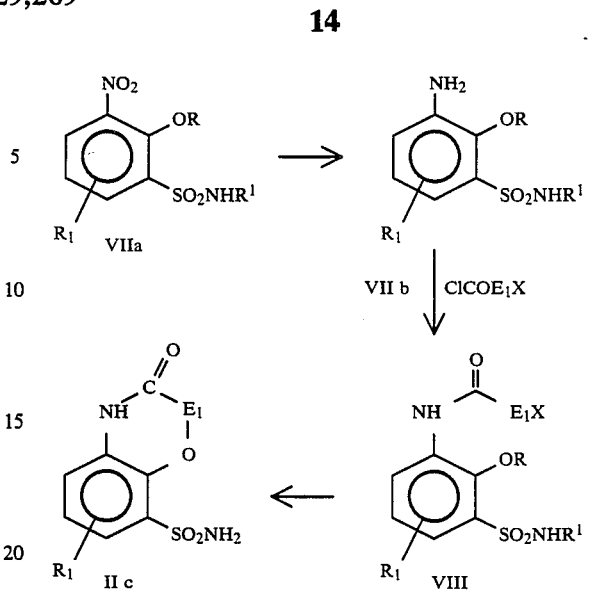

use of 3-nitro-2-alkoxybenzenesulfonamides VII. Reduction of the nitro group followed by acylation of the amino group gives acylamino benzene-sulfonamides VIII. In the case where R is hydrogen the heterocyclic ring system is readily formed by treatment of the compound VIII with a base. If R is an alkyl group in compound VIII then dealkylation with for example aluminium chloride is carried out before the cyclisation step.

Preparation of compounds of formula II in which R₂ is not hydrogen can be carried out by alkylation of the nitrogen using standard techniques.

(c) Another route to the sulfonamides II (E=O) involves

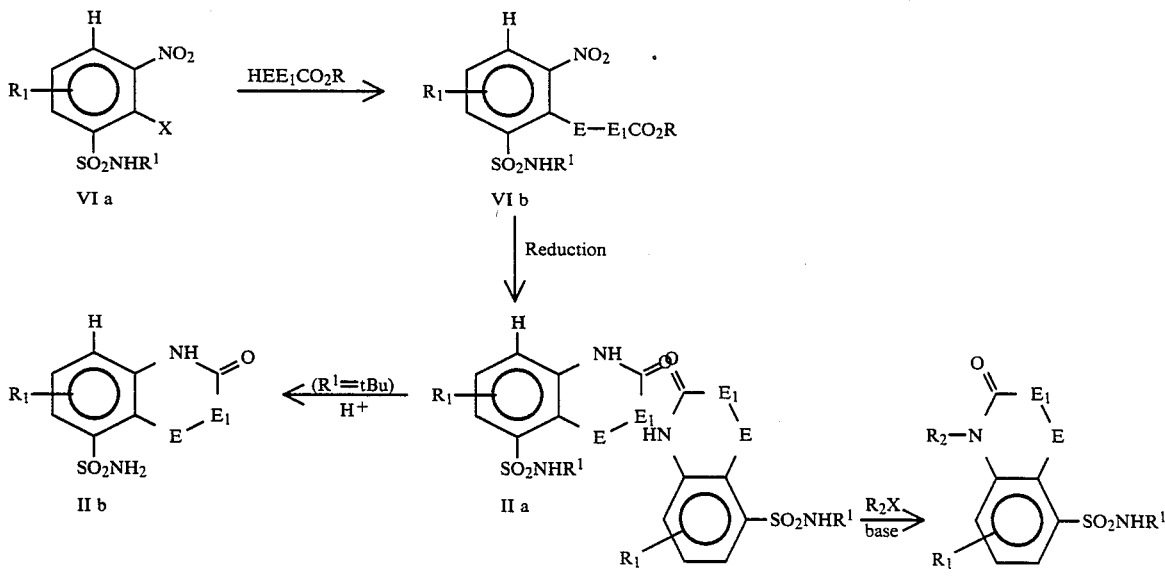

(e) Compounds of formula II in which $W_1$ is sulfur may be prepared from the corresponding oxygen compounds by treatment with reagents such as phosphorous pentasulfide and Lawessons reagent.

In each of parts (a), (b), (c) and (d) above group R may be either hydrogen or an alkyl group and group $R^1$ is either hydrogen or a tertiary butyl group.

In parts (b), (c) and (d) substituent X is a leaving group preferably a halogen atom.

Part B of the preparation of the compounds of the invention involves the preparation of the various nitrogen-containing heterocycles A-1 to A-7.

The heterocyclic amines of Formula IX can be prepared by methods known in the literature, or simple modifications thereof, by one skilled in the art.

       IX

For a review of the synthesis and reactions of 2- amino- and 2-methylaminopyrimidines (IX, A=A-1, Z=CH) see *The Chemistry of Heterocyclic Compounds, Vol.* 16, Wiley-Interscience, New York (1962). For a review of the synthesis and reactions of 2-amino- and 2-methylamino-s-triazines (IX, A=A-1, Z=N) see *The Chemistry of Heterocyclic Compounds, Vol.* 13, Wiley-Interscience, New York (1959), and F. C. Schaefer and K. R. Huffman, *J. Org. Chem.*, 28, 1812 (1963). EP-A No. 84,224 and W. Braker et al., *J. Amer. Chem. Soc.*, 69, 3072 (1947) describes methods for preparing aminopyrimidines and triazines substituted by acetal groups such as dialkoxymethyl or 1,3-dioxolan-2-yl. U.S. Pat. No. 4,515,626 describes methods for the synthesis of cyclopropyl-pyrimidines and triazines substituted by such groups as alkyl, haloalkyl, alkoxy, haloalkoxy, alkylamino, dialkylamino or alkoxyalkyl.

The 5,6-dihydrofuro[2.3-d]pyrimidine-2-amines, the cyclopenta[d]pyrimidines-2-amines (IX, A is A-2) and the 6,7-dihydro-5H-pyrano[2,3-d]pyrimidin-2-amines (IX, A is A-3) can be prepared as taught in U.S. Pat. No. 4,339,267. The furo[2,3-d]pyrimidin-2-amines (IX, A is A-4) are described in U.S. Pat. No. 4,487,626.

Compounds of formula IX where A is A-5, are described in EP-A-73,562. Compounds of Formula I where A is A-6, are described in U.S. Pat. No. 4,496,392.

The amines of Formula IX where A is A-7 can be prepared by methods taught in European Publication No. 125,864 (published 21/11/84) or by suitable modifications that would be obvious to one skilled in the art.

Part C of the preparation of the compounds of the invention (formula I) involves the coupling of the sulfonamides of formula II with the heterocyclic amines of formula IX. The compounds of formula I can be prepared by one or more of the methods described below.

(a) Many of the compounds of formula I can be prepared by reacting a sulfonylisocyanate or a sulfonylisothiocyanate of formula X with a heterocyclic amine of formula IX.

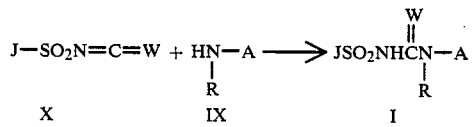

where J represents the bicyclic system

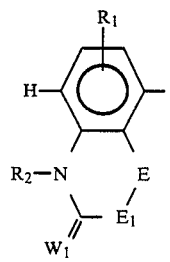

and W, A and R are as previously defined.

The reaction is carried out at 25° to 100° C. in an inert, aprotic solvent such as methylene chloride or xylene for 0.5 to 24 hours as taught in U.S. Pat. No. 4,127,405.

The intermediate sulfonylisocyanates (X, W=O) and isothiocyanates (X, W=S) are prepared by a variety of methods which are well known in the art and are described for example in European Patent Application 212,779 and the references cited therein.

Many of the compounds of formula I, where W is oxygen, can be prepared by reacting a phenyl carbamate of formula XI with a suitable amine of formula IX.

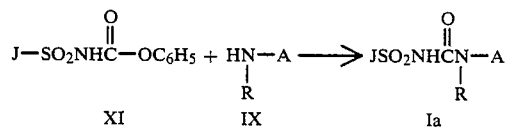

The reaction is carried out at 50° to 100° C. in a solvent such as dioxane for 0.5 to 24 hours. The required carbamates XI are prepared by reacting the corresponding sulfonamides II with diphenylcarbonate in the presence of a strong base.

(c) Compounds of formula Ia can also be made by reacting a heterocyclic carbamate of formula XII with a suitable sulfonamide of formula II.

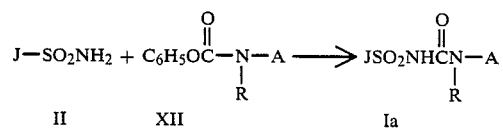

The reaction is carried out at 0° to 100° C. in a solvent such as acetonitrile or dioxane in the presence of a non-nucleophilic base such as DBU for 0.2 to 24 hours. The required phenylcarbamates XII are prepared by reacting the corresponding heterocyclic amines IX with diphenylcarbonate or phenylchloroformate in the presence of a strong base.

(d) Some of the compounds of the invention of formula Ib can be prepared by reacting a sulfonamide II with a heterocyclic isothiocyanate of formula XIII.

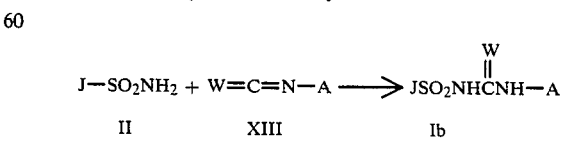

The reaction is carried out at 25° to 80° C. in an inert, aprotic solvent such as acetone or acetonitrile in the presence of a base such as potassium carbonate for 0.5 to 24 hours. The required heterocyclic isocyanates and iso-thiocyanates XIII are prepared from the corresponding amines H₂NA which would be known to one skilled in the art as taught in EPO Publication 35,893.

In each of parts (b), (c) and (d) above the groups J, W, A and R are as previously described.

Certain of the intermediate compounds of formulae II, III VI, VII and VIII are novel compounds and therefore in further embodiments the invention provides novel compounds of formulae II, III, VI, VII and VIII and processes for the preparation thereof.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g. hydroxide, alkoxide, carbonate or hydroxide). Quaternary amine salts can be made by similar techniques.

Salts of compounds of Formula I can also be prepared by exchange of one cation to another. Cationic exchange can be effected by direct treatment of an aqueous solution of a salt of a compound of Formula I, (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I, (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium sodium or calcium salt.

Acid addition salts, useful in this invention, can be obtained by reacting a compound of Formula I, with a suitable acid, e.g., p-toluenesulfonic acid, trichloroacetic acid or the like.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

The compounds of formula I may be applied directly to the plant (post-emergence application) or to the soil before the emergence of the plant (pre-emergence application).

Generally speaking the compounds of the present invention are highly active pre-emergent and especially post-emergent herbicides. Some of them have utility for broad spectrum total vegetation control. Other compounds of the invention have utility for selective weed control in crops such as sugar beet, soya bean, cotton and rice.

Accordingly, in yet a further aspect the invention provides a process for controlling weeds in cultivated crops which process comprises applying to the crop, or to the growth medium of the crop, a compound of formula I, as hereinbefore defined, in an amount sufficient to severely damage or kill the weeds but insufficient to damage the crop substantially.

Certain of the compounds of formula I exhibit useful plant growth regulating activity.

Plant growth regulating effects may be manifested in a number of ways. For example, suppression of apical dominance, stimulation of auxiliary bud growth, stimulation of early flowering and seed formation, enhancement of flowering and increase in seed yield, stem thickenings, stem shortening and tillering.

Accordingly in a still further aspect the invention provides a process for regulating the growth of a plant which process comprises applying to the plant, to the seed of the plant, or to the growth medium of the plant, an effective amount of a compound of formula I, as hereinbefore defined.

To effect the plant growth regulating process of the present invention the compounds of formula I may be applied directly to the plant (post-emergence application) or to the seed or soil before the emergence of the plant (pre-emergence) application.

The compounds of formula I may be used on their own to regulate the growth of plants but in general are preferably used in the form of a composition comprising a compound of the invention in admixture with a carrier comprising a solid or liquid diluent. Therefore, in a still further aspect the invention provides plant growth regulating compositions comprising a compound of formula I as hereinbefore defined and an inert carrier therefor.

The compositions of the present invention may be in the form of solids, liquids or pastes. The compositions include both dilute compositions which are ready for immediate use and concentrated compositions which may require dilution before use. Therefore, the concentration of the active ingredient in the compositions of the present invention will vary depending on the types of formulation and whether the composition is ready for use such as, for example, a dust formulation or an aqueous emulsion or whether the composition is a concentrate such as, for example, an emulsifiable concentrate or a wettable powder, which is suitable for dilution before use. In general, the composition of the present invention comprise from 1 ppm to 99% by weight of active ingredient.

The solid compositions may be in the form of powders, dusts, pellets, grains, and granules wherein the active ingredient is mixed with a solid diluent. Powders and dusts may be prepared by mixing or grinding the active ingredient with a solid carrier to give a finely divided composition. Granules, grains and pellets may be prepared by bonding the active ingredient to a solid carrier, for example, by coating or impregnating the preformed granular solid carrier with the active ingredient or by agglomeration techniques.

Examples of solid carriers include: mineral earths and clays such as, for example, kaolin, bentonite, kieselguhr, Fuller's earth, Attaclay, diatomaceous earth, bole, loess, talc, chalk, dolomite, limestone, lime, calcium carbonate, gypsum, calcium sulfate, pyrophyllite, silicic acid, silicates and silica gels, fertilizers such as, for example, ammonium sulfate, ammonium phosphate, ammonium nitrate and urea; natural products of vegetable origin such as, for example, grain meals and flours, bark meals, wood meals, nutshell meals and cellulosic powders; and synthetic polymeric materials such as, for example, ground or powdered plastics and resins.

Alternatively, the solid compositions may be in the form of dispersible or wettable dusts, powders, granules or grains wherein the active ingredient and the solid carrier are combined with one or more surface active agents which act as wetting, emulsifying and/or dispersing agents to facilitate the dispersion of the active ingredient in liquid.

Examples of surface active agents include those of the cationic, anionic and non-ionic type. Cationic surface active agents include quaternary ammonium compounds, for example, the long chain alkylammonium salts such as cetyltrimethylammonium bromide. Anionic surface active agents include: soaps or the alkali metal, alkaline earth metal and ammonium salts of fatty acids; the alkali metal, alkaline earth metal and ammonium salts of ligninsulfonic acid; the alkali metal, alkaline earth metal and ammonium salts of arylsulfonic acids including the salts of naphthalenesulfonic acids such as butylnaphthalenesulfonic acids, the di- and tri-isopropylnaphthalenesulfonic acids, the salts of the condensation products of sulfonated naphthalene and naphthalene derivatives with formaldehyde, the salts of the condensation products of sulfonated naphthalene and naphthalene derivatives with phenol and formaldehyde, and the salts of alkylarylbenzenesulfonic acids such as dodecylbenzenesulfonic acid; the alkali metal, alkaline earth metal and ammonium salts of the long chain mono esters of sulfuric acid or alkylsulfates such as laurylsulfate and the mono esters of sulfuric acid with fatty alcohol glycol ethers. Nonionic surface active agents include: the condensation products of ethylene oxide with phenols and alkylphenols such as isooctylphenol, octylphenol and nonylphenol; the condensation products of ethylene oxide with castor oil; the partial esters derived from long chain fatty acids and hexitol anhydrides, for example sorbitan monolaurate, and their condensation products with ethylene oxide; ethylene oixde/propylene oxide block copolymers; lauryl alcohol polyglycol ether acetal; and the lecithins.

The liquid compositions may comprise a solution or dispersions of the active ingredient in a liquid carrier optionally containing one or more surface active agents which act as wetting, emulsifying and/or dispersing agents. Examples of liquid carriers include: water, mineral oil fractions such as, for example, kerosene, solvent naphtha, petroleum, coal tar oils and aromatic petroleum fractions; aliphatic, cycloaliphatic and aromatic hydrocarbons such as, for example, paraffin, cyclohexane, toluene, the xylenes, tetrahydronaphthalene and alkylated naphthalenes; alcohols such as, for example, methanol, ethanol, propanol, isopropanol, butanol, cyclohexanol and propylene glycol; ketones such as, for example, dimethylformamide, dimethysulfoxide, N-methylpyrrolidone and sulfolane.

A preferred liquid composition comprises an aqueous suspension, dispersion or emulsion of the active ingredient which is suitable for application by spraying, atomizing or watering. Such aqueous compositions are generally prepared by mixing concentrated compositions with water. Suitable concentrated compositions include emulsion concentrates, pastes, oil dispersions, aqueous suspensions and wettable powders. The concentrates are usually required to withstand storage for prolonged periods and after such storage to be capable of dilution with water to form aqueous preparations which remain homogeneous for a sufficient time to enable them to be applied by conventional spray equipment. The concentrates conveniently contain from 10 to 99%, preferably 10 to 60%, by weight of active ingredient.

Emulsion or emulsifiable concentrates are conveniently prepared by dissolving the active ingredient in an organic solvent containing one or more surface active agents and optionally an oil. Oil dispersions may be prepared by grinding together the active ingredient, a hydrocarbon oil, and one or more surface active agents. Aqueous suspension concentrates may conveniently be prepared by ball milling a mixture of the active agent and preferably at least one suspending agent. Suitable suspending agents include: hydrophilic colloids such as, for example, poly(N-vinylpyrrolidone), sodium carboxymethylcellulose and the vegetable gums, gum acacia and gum tragacanth; hydrated colloidal mineral silicates such as, for example, montmorillonite, beidellite, nontronite, hectorite, saponite, sauconite and bentonite; other cellulose derivatives; and poly(vinyl alcohol). Wettable powder concentrates may conveniently be prepared by blending together the active ingredient, one or more surface active agents, one or more solid carriers and optionally one or more suspending agents and grinding the mixture to give a powder having the required particle size.

The aqueous suspensions, dispersions or emulsions may be prepared from the concentrated compositions by mixing the concentrated compositions with water optionally containing surface active agents and/or oils.

It should be noted that the compounds of the invention of formula I are acidic. Therefore, the compounds of formula I may be formulated and applied as the salts of organic or inorganic bases. In formulating and employing the compounds of formula I in the form of their salts either the salts per se may be used in the formulation or the compounds of formula I may be used in the formulation and the salts generated in situ by the use of the appropriate organic or inorganic base.

The mode of application of the compositions of the invention will depend to a large extent on the type of composition used and the facilities available for its application. Solid compositions may be applied by dusting or any other suitable means for broadcasting or spreading the solid. Liquid compositions may be applied by spraying, atomizing, watering, introduction into the irrigation water, or any other suitable means for broadcasting or spreading the liquid.

The rate or application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.001 to 10 kilograms per hectare is suitable while from 0.01 to 5.0 kilogram per hectare may be preferred.

The composition of the invention may comprise, in addition to one or more compounds of the invention, one or more compounds not of the invention but which possess biological activity. As a result, in certain applications the herbicidal use of the compounds of the invention alone may not be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

The compounds of this invention and their preparation are further illustrated by the following examples.

Example 1

(i) 5-t-butyl-2-methoxy-3-nitrophenylsulfonyl chloride

Concentrated sulphuric acid (13 ml) was added dropwise to a cooled mixture of 5-t-butyl 2-methoxyphenylsulfonyl chloride (9.0 g) and potassium nitrate (6.90 g) in dichloromethane (100 ml). The reaction mixture was then stirred for 16 hours at ambient temperature. The mixture was then poured onto ice-cold water (200 ml) and the organic layer was separated and dried over sodium sulphate. Removal of solvent gave the title compound as a pale yellow solid (9.1 g).

$^1$H NMR (CDCl$_3$): δ 1.4 (s, 9H); 4.1 (s, 3H); 8.2 (s, 2H).

(ii) 5-t-butyl-2-methoxy-3-nitrophenyl N-t-butyl sulfonamide t-Butylamine (9 ml) was added to a cooled solution of 5-t-butyl-2-methoxy-3-nitrophenyl sulfonyl chloride (7.4 g) in acetonitrile (40 ml). The mixture was stirred at ambient temperature for 1 hour and then the solvent was removed under vacuum. The residue was shaken with ethyl acetate (100 ml) and 4% citric acid (100 ml). The organic phase was separated and dried over sodium sulphate. Evaporation of solvent gave a solid residue which was recrystallized from aqueous ethanol to give the title compound (6.0 g);

$^1$H NMR (CDCl$_3$): δ 1.2 (s, 9H); 1.4 (s, 9H); 4.1 (s, 3H); 8.0 (d, 1H); 8.2 (d, 1H).

(iii) 5-t-butyl-2-methoxy-3-aminophenyl N-t-butyl sulfonamide

Ammonium formate (8.0 g) was added to a stirred and cooled mixture of 5-t-butyl-2-methoxy-3-nitrophenyl N-t-butyl-sulfonamide (8.0 g) and 10% Palladium on charcoal (1.1 g) in dry methanol (80 ml) under nitrogen. The mixture was stirred at ambient temperature for 1 hour and then filtered through diatomaceous earth. The filtrate was concentrated and taken up into a mixture of ethyl acetate and water. The organic layer was separated and dried over sodium sulphate. After removal of solvent and recrystallization from aqueous ethanol the title compound was obtained as white crystals (6.9 g).

$^1$H NMR (CDCl$_3$): δ 1.17 (s, 9H); 1.29 (s, 9H); 3.7 (s, 2H); 3.9 (s, 3H); 5.0 (s, 1H); 7.0 (d, 1H); 7.3 (d, 1H);

(iv) 5-t-butyl-2-methoxy-3-(chloroacetamido) phenyl N-t-butylsulfonamide

A solution of chloroacetyl chloride (4.4 ml) in dichloromethane (40 ml) was added dropwise to a cooled and stirred solution of 5-t-butyl-2-methoxy-3-aminophenyl N-t-butyl-sulfonamide (15.6 g) and diisopropylethylamine (9.5 ml) in dichloromethane (100 ml). The solution was left standing at ambient temperature for 2 hours and then washed with a 2% solution of citric acid. The organic phase was dried and evaporated. Recrytallization from aqueous ethanol gave the title compound (16.4 g).

$^1$H NMR (CDCl$_3$): δ 1.19 (s, 9H); 1.33 (s, 9H); 4.0 (s, 3H) 4.3 (s, 2H); 5.0 (s, 1H) exch. 7.7 (d, 1H); 8.6 (d, 1H); 8.8 (s, 1H) exch.

(v) 3-(Chloroacetamido)-2-hydroxyphenyl sulfonamide

A mixture of 5-t-butyl-2-methoxy-3-(chloroacetamido) phenyl-N-t-butyl-sulfonamide (8.0 g), aluminium chloride (16.4 g) and m-xylene (80 ml) was heated at 95° C. with stirring for 16 hours under nitrogen. The mixture was then poured into a beaker containing diethyl ether (300 ml) and water (300 ml) and stirred at ambient temperature for 15 minutes. The organic layer is separated and dried over sodium sulphate and concentrated under vacuum in order to remove all diethyl ether. The residual solution was cooled and hexane added to precipitate the title compound (4.7 g).

$^1$H NMR (CDCl$_3$/DMSO): δ 4.26 (s, 2H); 5.83 (bs, 3H) exch.; 6.91 (t, 1H); 7.54 (dd, 1H); 8.05 (dd, 1H); 9.5 (s, 1H).

(vi) 8-Sulfonamido-2H-1,4-benzoxazin-3 (4H)-one

A mixture of 3-(chloroacetamido)-2-hydroxyphenylsulfonamide (2.4 g) and potassium carbonate (1.50 g) in acetone (100 ml) was stirred and heated under reflux for 1 hour. Acetone was removed under vacuum and 4% aqueous citric acid (50 ml) was added. Filtration gave the crude product which was triturated with ethyl acetate and again filtered to give the title compound (1.66 g).

$^1$H NMR (d6 DMSO): δ 4.68 (s,2H); 6.9–7.4 (m, 3H); 7.26 (s, 2H); 10.9 (s, 1H).

(vii) 8-(Phenoxycarbonylsulfonamido)-2H-1,4-benzoxazin-3(4H)-one

Sodium hydride (0.13 g) was added to a cooled solution of 8-sulfonamido-2-H-1,4-benzoxazin-3(4H)-one (1.0 g) in dimethyl formamide (10 ml). After stirring the cooled solution for 15 minutes diphenyl carbonate (1.13 g) was added and the mixture was stirred at ambient temperature for 16 hours. Ethyl acetate and 4% citric acid were added and the organic phase was washed three times with brine. The dried ethyl acetate solution was concentrated and the residue trituated with ether to give the title compound (1.1 g) as a white solid.

$^1$H NMR (d6 DMSO): δ 3.4 (s, 1H); 4.8 (s, 2H); 6.6–7.5 (m, 8H); 11.0 (s, 1H).

(viii) N-[(4-Methoxy-6-methylpyrimidin-2-yl) amino carbonyl]-2H-1,4-benzoxazin-3(4H)-one-8-sulfonamide (2)

A mixture of 8-(phenoxy carbonylsulfonamido)-2H-1,4-benzoxazin-3(4H)-one (1.1 g) and 2-amino-4-methoxy-6-methylpyrimidine (0.44 g) in dioxane (20 ml) was heated under reflux for 1.5 hour. The mixture was then cooled and diethyl ether (20 ml) was added. Filtration gave a white solid (0.90 g). The solid was suspended in ethyl acetate (100 ml) and the suspension was twice extracted with sodium carbonate solution (100 ml). The combined carbonate extract was acidified and the resulting precipitate was filtered to give the title compound (0.37 g).

$^1$H NMR (d6 DMSO): 2.34 (s, 3H); 3.54 (s, 1H) exch.; 3.94 (s, 3H); 4.51 (s, 2H); 6.54 (s, 1H); 6.91–7.50 (m, 3H); 10.5 (s, 1H) exch.; 11.1 (s, 1H) exch.

Example 2

(i) 5-Bromo-2-hydroxy-3-nitro-t-butylbenzenesulphonamide

A solution of 5-Bromo-2-hydroxy benzenesulfonylchloride (50 g) in dichloromethane (200 ml) was added dropwise to a cooled, stirred solution of conc. nitric acid (20 ml) and conc. sulphuric acid (20 ml). The mixture was then allowed to come to room temperature and stirred for another 2 hours. The reaction mixture was quenched with ice-water and the organic layer was separated and washed with brine, and then dried over MgSO4. The dried solution was cooled in ice and t-butylamine (50 ml) was added dropwise. The mixture was stirred at room temperature for an other 2 hours before it was shaken with citric acid solution. The organic layer was dried and concentrated to a yellow solid. Recrystallization from aqueous ethanol gave pure 5-bromo-2-hydroxy-3-nitro-t-butyl-benzenesulfonamide (19 g).

$^1$H NMR (CDCl$_3$): δ 1.3 (s,9H); 5.1 (s, 1H) exch.; 8.3–8.5 (m, 2H).

(ii) 3-amino-2-hydroxy-t-butylbenzenesulphonamide

A mixture of 5-bromo-2-hydroxy-3-nitro-t-butylbenzenesulfonamide (7.1 g) and ammonium formate (10 g) in methanol (70 ml) was stirred, cooled in ice and kept under nitrogen for 15 minutes before addition of 10% Palladium on charcoal (0.70 g). The mixture was subsequently stirred at ambient temperature for 18 hours. The catalyst was filtered off and the filtrate was concentrated to a black residue. The residue was dissolved in a mixture of water and ethyl acetate. The organic layer was dried and concentration gave a 3-amino-2-hydroxy-t-butylbenezene sulphonamide (5.7 g) as a black oil.

$^1$H NMR (α6 Acetone) δ 1.1 (s, 9H); 6.6–7.1 (m, 3H).

(iii) 8-t-butylsulfonamido-2H-1,4-benzoxazin-3-(4H)-one

Chloroacetyl chloride (6.7 ml) was added slowly to an ice-cooled mixture of 3-amino-2-hydroxy-t-butylbenzenesulfonamide (15.5 g), sodiumbicarbonate (14.6 g), water (45 ml) and isobutylmethyl ketone (45 ml). The mixture was allowed to come to ambient temperature and was stirred for at least 2 hours. The mixture was then heated under reflux for 4 hours. The mixture was cooled, concentrated and triturated with ethyl acetate (200 ml). The solid was filtered and stirred in water before being filtered again. The dried solid was the desired 8-t-butylsulfonamido-2H-1,4-benzoxazin-3(4H)-one (10.1 g).

$^1$H NMR (d6 DMSO) δ 1.1 (s, 9H); 4.7 (s, 2H); 6.9–7.5 (m, 5H); 11.0 (S, 1H) exch.

(iv) 4-Methyl-8-t-butylsulfonamido-2H-1,4-benzoxazin-3(4H)-one

A mixture of 8-t-butylsulfonamide-2H-1,4-benzoxazin-3(4H)-one (2.0 g), potassium carbonate (1.5 g) and methyl iodide (8 ml) was heated to reflux for 18 hours. The mixture was concentrated under vacuum and the residue was dissolved in ethyl acetate and dilute aqueous citric acid. The dried organic phase gave pure 4-methyl-8-t-butyl-sulfonamido-2H-1,4-benzoxazin-3(4H)-one (1.8 g) as a solid.

$^1$H NMR (CDCl$_3$) δ 1.3 (s, 9H); 3.4 (s, 3H); 4.7 (s, 2H); 5.0 (s, 1H) exch.; 7.0–7.7 (m, 3H).

(v) 4-Methyl-8-sulfonamido-2H-1,4-benzoxazin-3(4H)-one

A solution of 4-methyl-8-t-butylsulfonamido-2H-1,4-benzoxazin-3(4H)-one (5.5 g) in trifluoroacetic acid (20 ml) was heated at 60°–70° C. for 2 hours. The solution was concentrated under vacuum and triturated with ethyl acetate and diethyl ether to give solid 4-methyl-8-sulfonamido-2H-1,4-benzoxazin-3(4H)-one (3.3 g).

$^1$H NMR (DMSO/CDCl$_3$) δ 3.4 (s, 3H); 4.7 (s,2H); 6.9(S,2H) exch.; 7.0–7.6 (m, 3H).

(vi) N-[(4-Methoxy-6-methylpyrimidin-2-yl) amino carbonyl]-4-methyl-2H-1,4-benzoxazin-3-one-8-sulfonamide (25)

Reaction of the sulfonamide from part (v) according to the conditions given in Example 1 parts (vii) and (viii) gave the sulfonyl urea, compound No. 25. The compound was characterised by thin layer chromatography, infrared and proton magnetic resonance spectroscopy. The PMR spectral data is given in Example 10, Table 2.

Example 3

(i) 4-Methyl-8-sulfonamido-2H-1,4-benzoxazin-3-thione

A mixture of the benzoxazinone from Example 2, part (v) (0.50 g) and phosphorus pentasulfide (0.47 g) in pyridine (3 ml) was heated under reflux for 1 hour. The mixture was cooled, ethyl acetate was added and the solution was washed three times with dilute aqeuous citric acid (100 ml). The dried organic layer gave the thio-amide (0.38 g) as a solid.

$^1$H NMR (DMSO/CDCl$_3$) δ 3.8 (s, 3H); 5.0 (s, 2H); 6.4 (s, 2H, exch.); 7.0–7.7 (m, 3H).

(ii) N-[(4-Methoxy-6-methylpyrimidin-2yl) amino carbonyl]-4-Methyl-2H-1,4-benzoxazin-3-thione-8-sulfonamide (27)

The above sulphonamide (0.50 g) was added to a mixture of 4-methoxy-6-methylpyrimidin-2-yl phenyl carbonate (1.5 g) and 1,8-diazobicyclo [5.4.0] undec-7 ene (0.8 ml) in acetonitrile (10 ml) and stirred at ambient temperature for 18 hours. The mixture was acidified with citric acid solution and the product was extracted into ethyl acetate. The residue of the dried organic layer was triturated with ethyl acetate to give compound No. 27 (0.15 g).

$^1$H NMR (CDCl$_3$) δ 2.5 (s, 3H); 3.8 (s, 3H); 3.9 (s, 3H); 4.9 (s, 2H); 6.3 (s, 1H) 6.9–8.0 (m, 3H).

Example 4

(i) Addition of thioglycolic acid to 4-chloro-3,5-dinitrobenzotrifluoride

Thioglycolic acid (5.46 ml, 0.078 mole) was added to a stirred suspension of sodium carbonate (16.72 g, 0.16 mole) and 4-chloro-3,5-dinitrobenzotrifluoride (19.4 g, 0.072 mole) in ethanol (100 ml). The reaction mixture was stirred at room temperature overnight and the resulting solid mass diluted with ether (250 ml) acidified with 5M hydrochloric acid (100 ml).

The ether extract was washed successively with 1M hydrochloric acid (1×) and saturated sodium chloride (2×), dried (Na$_2$SO$_4$) and concentrated to afford an orange solid of the thiophenoxy acetic acid (23.4 g, 100%).

(CDCl$_3$) δ:8.18 (s, 2H); 3.75 (s, 2H).

(ii) 8-Amino-3-oxo-6-trifluoromethyl-3,4-dihydro-2H-1,4-benzothiazine

Concentrated hydrochloric acid (200 ml) was added slowly down a condenser to an ice-bath cooled solution of the thiophenoxyacetic acid from part (i) (17.92 g, 0.055 mole) and tin metal (powder, 72 g) in ethanol (40 ml).

The initially orange reaction solution was then heated on a boiling steam bath for 30 mins. before cooling to room temperature. The resulting colourless solution was then poured slowly into a stirring ice-bath cooled solution of aqueous sodium hydroxide (250 g in 500 ml) and stirring continued for 15 mins, until the initial colourless precipitate had effectively dissolved. The suspension was extracted into ether (4×300 ml) and the combined extracts washed with saturated sodium chloride (3×), dried (Na$_2$SO$_4$) and concentrated to afford a colourless solid. The solid was dissolved in a small volume of ethyl acetate/ether (1:1) and filtered through a short plug of silica to yield the benzothiazine as a colourless solid (10.09 g, 74%).

(CDCl$_3$/DMSO) δ 10.43 (brs, 1H); 6.68 and 6.63, (2×s, 2H); 4.20 (brs, 2H); 3.35 (s, 2H).

(iii) 3-Oxo-8-sulphonamido-6-trifluoromethyl-3,4-dihydro-2H-1,4-benzothiazine

A solution of sodium nitrite (1.41 g, 20.5 mmole) in water (5 ml) was added dropwise over 5 min to a cooled (−5°) solution of the benzothiazine amine (5.04 g, 20.30 mmole) in concentrated hydrochloric acid (20 ml) and acetic acid (6 ml).

Following 15 mins. stirring, the gold-brown solution of the diazonium salt was added to a stirred solution of cuprous chloride (200 mg) in acetic acid (40 ml) saturated with sulphur dioxide, all at 0°. The ice-bath was removed after 5 min and the solution allowed to warm to room temperature and stir for a further 90 min. The resulting transparent green reaction mixture was poured into ice/water, extracted into ethyl acetate, washed with saturated sodium chloride (3×), dried (Na$_2$SO$_4$) and concentrated to afford the sulphonyl chloride as a pale tan solid.

$^1$H(CDCl$_3$) δ 10.78 (brs, 1H); 8.07 (d, J=1.5 Hz, 1H); 7.52 (d, J=1.5 Hz, 1H); 3.58 (s, 2H).

The sulphonyl chloride was dissolved in dichloromethane (100 ml) cooled to −78° and a slow stream of dry ammonia gas was bubbled through the solution for 15 mins. The cooling bath was removed and the solution stirred at room temperature overnight to evaporate the excess ammonia. The solvent was then evaporated and the resulting solid residue taken up into ethyl acetate and washed successively with water (1×) and saturated sodium chloride (3×), dried (Na$_2$SO$_4$) and concentrated to afford a tan solid. The crude solid was suspended in boiling ether and filtered to afford the sulphonamide as a colourless solid (4.16 g, 66%).

$^1$H (CDCl$_3$/DMSO) 11.01 (s, 1H); 7.85 (d, J=1.5 Hz, 1H); 7.44 (d, J=1.5 Hz, 1H); 7.26, (s, 2H); 3.41 (s, 2H).

(iv) N-[(4-Methoxy-6-methylpyrimid-2-yl)amino carbonyl]-6-trifluoromethyl-3,4-dihydro-2H-1,4-benzthiazin-3-(4H)-one-8-sulfonamide (11)

(4-Methoxy-6-methylpyrimid-2-yl)amino phenyl carbamate (0.32 g, 1.23 mmole) was added to a cooled (15°) solution of the benzothiazine sulphonamide from part (iii) (0.35 g, 1.12 mmole) and 1,8-diazobicyclo [5.4.0] undec-7-ene (0.19 g, 1.23 mmole) in dry 1,4-dioxane (10 ml). The solution was allowed to warm to room temperature and stirred overnight. The resulting suspension was diluted with ether and filtered to afford a colourless solid (0.65 g). The solid was dissolved in aqueous sodium carbonate and then acidified with aqueous citric acid to pH 4. The resulting solid was filtered, washed with cold water and dried to yield the sulphonyl urea compound No. 79 as a dense colourless powder (0.17 g, 32%).

$^1$H(DMSO) 14.13 (brs, 1H); 11.05 and 10.83 (2×s, 2H); 7.88 and 7.51 (2×s, 2H); 6.59 (s, 1H); 3.95, (s, 3H); 3.53 (s, 2H); 2.41 (s, 3H).

Example 5

Compound Nos. 1, 3, 26, 31, 32, 36, 37, 38, 39, 41, 45, 46, 49, 57, 115, 140, 147, 150, 151, 172, 181, 182, 183, 192, 193, 200, 204 and 239 were each prepared by coupling the appropriate benzoxazinone sulfonamide and 2-amino heterocycle. The coupling was generally carried out using the conditions described in Example 1, parts (vii) and (viii) or those described in Example 4, part (iv). The various substituted benzoxazinone-8-sulfonamides were prepared from the appropriate substituted phenol following similar reactions to those described in Example 1, parts (i) to (vi) and Example 2 parts (i) to (v).

$^1$H NMR spectral data for each of these compounds is given in Example 10, Table 2.

Example 6

Compound Nos. 28, 40, 169, 174 and 208 were prepared by coupling the various sulfonamides of benzoxazine-3-thione or benzthiazine-3-thione with the appropriate 2-aminoheterocycle.

Each of the thioamides was prepared using similar reaction conditions to those described in Example 3 parts (i) and (ii).

$^1$H NMR spectral data for each of these sulfonylureas is given in Example 10, Table 2.

Example 7

Compound Nos. 65, 66, 74, 78, 80, 148, 154, 175, 201, 205, 207, 208, 226 and 227 were each prepared starting from the appropriate chloro dinitrobenzene and following a similar procedure to the general reaction conditions given in Example 4, parts (i) to (iv). The products were identified by various techniques including thin-layer chromatography, infrared spectroscopy and nuclear magnetic resonance spectroscopy.

$^1$H NMR spectral data is given in Example 10, Table 2.

Example 8

Preparation of benzothiazine-S-oxides 3-chloroperoxybenzoic acid (90%, 82 mg, 0.43 mmole) was added to a cooled (10° C.) stirred solution of the sulphonyl urea compound No. 65 (160 mg, 0.39 mmole) in 1,4-dioxane (50 ml). The cold bath was removed and stirring continued for a further 5 min. The solvent was evaporated under reduced pressure and the oily residue triturated with a small volume of ethyl acetate (2 ml) and to the resulting suspension was added ether (20 ml). The suspension was filtered, washed with ether and dried to afford a colourless solid of the sulphoxide compound No. 84 (137 mg, 82%).

Compound Nos. 113, 156, 178 and 202 were each made by the above method starting from the appropriate benzothiazine sulfonylurea.

$^1$H NMR spectra data for each of these compounds is given in Example 10, Table 2.

Example 9

Preparation of benzothiazine-S,S-dioxides

The benzothiazine sulfonyl urea, compound No. 65 (185 mg, 0.45 mmole) was treated with 3-chloroperoxybenzoic acid (90%, 191 mg, 0.99 mmole) in dioxane (50 ml) as previously described except the solution was heated on a steam bath for 1.5 h. This resulted in the isolation of the sulphone, compound No. 98 (126 mg, 63%) as a colourless solid. The $^1$H NMR spectra data is recorded in Example 10, Table 2.

Example 10

TABLE 2

| Compound No. | Proton chemical Shift in ppm (d$_6$ DMSO) |
|---|---|
| 1 | 2.4 (s, 6 H); 4.5 (s, 2 H); 7.0 (s, 1 H) 6.8–7.5 (m, 3 H) |
| 3 | 3.9 (s, 6 H); 4.5 (s, 2 H); 5.9 (s, 1 H); 7.0–7.6 (m, 3 H); 8.2 (s, 1 H); 10.3 (bs, 1 H) 11.0 (bs, 1 H) |
| 7 | 4.7 (s, 2 H); 6.9–7.7 (5 H, m); 11.0 (s, 1 H) |
| 25 | (CDCl$_3$) 2.4 (s, 3 H); 3.3 (s, 3 H); 3.9 (s, 3 H); 4.6 (s, 2 H); 6.3 (s, 1 H); 7.1–7.4 (m, 2 H); 7.7–7.9 (m, 1 H) |
| 26 | (CDCl$_3$) 3.4 (s, 3 H); 4.0 (s, 6 H); 4.6 (s, 2 H); 5.8 (s, 1 H); 7.1–7.3 (m, 2 H); 7.5 (s, 1 H); 7.7–7.8 (m, 1 H); 12.8 (s, 1 H) |
| 28 | (CDCl$_3$) 3.8 (s, 3 H); 3.9 (s, 6 H); 4.9 (s, 2 H); 5.8 (s, 1 H); 7.1–7.5 (m, 3 H); 7.8 (dd, 1 H); 12.8 (s, 1 H) |
| 31 | 2.37 (s, 3 H); 3.91 (s, 3 H); 4.57 (s, 2 H); 6.54 (s, 1 H); 7.1 (m, 2 H); 10.57 (s, 1 H); 11.09 (s, 1 H); 13.49 (bs, 1 H) |
| 32 | 3.97 (s, 6 H); 4.61 (s, 2 H); 5.89 (s, 1 H); 7.14 (m, 2 H); exchangeable protons not observed |
| 36 | 3.26 (s, 3 H); 3.90 (s, 6 H); 4.66 (s, 2 H); 6.01 (s, 1 H); 7.39 (m, 2 H); 7.46 (s, 1 H); 10.57 (s, 1 H); 12.93 (s, 1 H) |
| 37 | 2.33 (s, 3 H); 3.23 (s, 3 H); 3.87 (s, 3 H); 4.61 (s, 2 H); 6.45 (s, 1 H); 7.31 (m, 2 H); 7.31 (s, 1 H); 10.00 (s, 1 H) |
| 38 | 2.41 (s, 3 H); 3.94 (s, 3 H); 4.61 (s, 2 H); 6.58 (s, 1 H); 7.12 (d, 1 H); 7.36 (d, 1 H); 10.5 (bs, 1 H); 11.1 (bs, 1 H); 13.2(bs, 1 H) |
| 39 | 3.92 (s, 6 H); 4.59 (s, 2 H); 5.95 (s, 1 H); 7.11 (d, 1 H); 7.34 (d, 1 H); 10.4 (s, 1 H); 11.0 (s, 1 H); 12.9 (bs, 1 H) |
| 40 | d$_6$ acetone 4.04 (s, 3 H); 4.99 (s, 2 H); 6.68 (s, 1 H); 7.43 (d, 1 H); 7.58 (d, 1 H); 9.6 (bs, 1 H) other exchangeables not observed |
| 41 | d$_6$ acetone 4.04 (s, 3 H); 4.71 (s, 2 H); 6.66 (s, 1 H); 7.2 (d, 1 H); 7.46 (d, 1 H); 9.6 (bs, 1 H); 10.0 (bs, 1 H); one exchangeable not observed; |
| 45 | 2.30 (s, 3 H); 2.44 (s, 3 H); 3.94 (s, 3 H); 4.40 (s, 2 H); 6.30 (s, 1 H); 6.94 (s, 1 H); 7.33 (s, 1 H); 9.6 (s, 1 H); 10.7 (bs, 1 H); 13.1 (bs, 1 H) |
| 46 | 2.30 (s, 3 H); 3.89 (s, 6 H); 4.44 (s, 2 H); 5.95 (s, 1 H); 6.95 (s, 1 H); 7.34 (s, 1 H); 9.5 (bs, 1 H); 10.6 (s, 1 H); 12.8 (bs, 1 H) |
| 49 | 1.23 (s, 9 H); 2.34 (s, 3 H); 3.93 (s, 3 H); 4.50 (s, 2 H); 6.45 (s, 1 H); 6.89 (s, 2 H); 9.23 (bs, 1 H); 10.53 (s, 1 H); 11.13 (s, 1 H) |
| 57 | 2.2 (s, 3 H); 2.4 (s, 3 H); 3.89 (s, 6 H); 4.4 (s, 2 H); 5.96 (s, 1 H); 6.93 (s, 1 H); 10.1 (bs, 1 H); 10.7 (bs, 1 H); 12.5 (bs, 1 H) |
| 65 | 2.39 (s, 3 H); 3.40 (s, 2 H); 3.93 (s, 3 H); 6.55 (s, 1 H); 7.2–7.8 (m, 3 H); 10.59 (s, 1 H); 10.86 (s, 1 H); 13.67 (bs, 1 H |
| 66 | 3.37 (s, 2 H); 3.97 (s, 6 H); 6.03 (s, 1 H); 7.0–744 (m, 3 H); 10.46 (s, 1 H); 10.74 (s, 1 H); 12.74 (bs, 1 H) |
| 74 | 2.4 (s, 3 H); 3.4 (s, 2 H); 3.9 (s, 3 H); 6.5 (s, 1 H); 7.4–7.7 (m, 3 H); 10.2 (bs, 1 H); 12.8 (bs, 1 H) |
| 78 | 2.4 (s, 3 H); 3.5 (s, 2 H); 3.9 (s, 3 H); 7.3 (d, J = 2.1 Hz, 1 H); 7.6 (d, 1 H) 10.9 (bs, 2 H); 12.5 (bs, 1 H) |
| 80 | 2.4 (s, 3 H); 3.4 (s, 5 H); 3.9 (s, 3 H); 6.5 (s, 1 H); 7.6 (d, 1 H); 7.7 (d, 1 H) 10.6 (bs, 1 H); 11.1 (bs, 1 H) |
| 84 | 2.41 (s, 1 H); 3.93 (s, 3 H); 4.17 (s, 2 H); 6.58 (s, 1 H); 7.0–7.9 (m, 3 H); 10.7 (s, 1 H); 11.2 (s, 1 H); 14.0 (bs, 1 H) |
| 98 | 2.38 (s, 3 H); 3.94 (s, 3 H); 4.83 (s, 2 H); 6.53 (s, 1 H); 7.10–7.95(m, 3 H); 10.61 (s, 1 H); 11.42 (s, 1 H); 13.5 (bs, 1 H) |
| 113 | 2.45 (s, 6 H); 4.22 (s, 2 H); 7.07 (s, 1 H); 7.47 (d, 1 H); 7.69 (d, 1 H); 10.9 (bs, 1 H); 11.3 (bs, 1 H); 13.0 (bs, 1 H) |
| 114 | 2.40 (s, 6 H); 3.42 (s, 2 H); 6.99 (s, 1 H); 7.26 (d, 1 H); 7.62 (d, 1 H); 10.6 (s, 1 H); 10.93 (s, 1 H); 13.88 (bs, 1 H) |
| 115 | 2.5 (s, 3 H); 4.0 (s, 3 H); 4.6 (s, 2 H); 6.9–7.5 (m, 3 H); 10.8 (s, 1 H); 11.0 (s, 1 H); 12.5 (s, 1 H) |
| 140 | 2.5 (s, 3 H); 3.3 (s, 3 H); 4.0 (s, 3 H); 4.7 (s, 2 H); 6.9–7.7 (m, 3 H); 10.9 (s, 1 H); 12.6 (s, 1 H) |
| 147 | 2.5 (s, 3 H); 3.9 (s, 3 H); 4.6 (s, 2 H); 7.1 (d, 1 H); 7.3 (d, 1 H); 9.2 (bs, 1 H); 11.0 (bs, 1 H); 13.0 (bs, 1 H) |
| 148 | 2.4 (s, 3 H); 3.5 (s, 2 H); 3.9 (s, 3 H); 7.3 (d, 1 H); 7.6 (d, 1 H); 11.0 (bs, 1 H); other exchangeables not observed |
| 150 | 1.3 (d, J = 6 Hz, 3 H); 2.4 (s, 3 H); 3.9 (s, 3 H); 4.7 (q, 1 H); 6.6 (s, 1 H); 6.9–7.6(m, 3 H); 10.5 (s, 1 H); 10.9 (s, 1 H); 13.2 (s, 1 H) |
| 151 | 1.3 (d, J = 6 Hz, 3 H); 3.8 (s, 6 H); 4.7 (q, 1 H); 5.7 (s, 1 H); 6.9–7.6 (m, 3 H); 9.1 (s, 1 H); 10.8 (s, 1 H); 12.9 (s, 1 H) |
| 154 | 1.0 (d, J = 7 Hz, 3 H); 2.5 (s, 3 H); 3.5 (q, 1 H); 3.9 (s, 3 H); 6.5 (s, 1 H); 7.2–7.8 (m, 3 H); 10.5 (s, 1 H); 10.9 (bs, 1 H); 13.7 (bs, 1 H) |
| 156 | 1.0 and 1.1 (2 d, J = 7 Hz, 3 H); 2.3 (s, 3 H); 4.0 (s, 3 H); 4.1 (q, 1 H); 6.5 (s, 1 H); 7.3–7.7 (m, 3 H); 11.1 (bs, 1 H); other exchangeables not observed |
| 159 | d$_6$ acetone 1.7 (s, 6 H); 2.5 (s, 3 H); 4.0 (s, 3 H); 6.5 (s, 1 H); 7.0–7.8 (m, 3 H); 10.2 (s, 1 H); 10.8 (s, 1 H); 13.2 (s, 1 H) |
| 160 | d$_6$ acetone 1.7 (2, 6 H); 4.0 (s, 6 H); 5.9 (s, 1 H); 6.9–7.7 (m, 3 H); 10.2 (s, 1 H); 10.7 (s, 1 H); 12.9 (s, 1 H) |
| 162 | d$_6$ acetone 2.2 (s, 3 H); 3.9 (s, 3 H); 5.8 (s, 1 H); 6.3 (s, 1 H); 7.0–7.8 (m, 8 H); 9.0 (s, 1 H); 10.2 (s, 1 H); 13.1 (s, 1 H) |
| 169 | 1.5 (d, J = 6 Hz, 3 H); 2.5 (s, 3 H); 4.0 (s, 3 H); 5.1 (q, 1 H); 6.5 (s, 1 H); 6.9–7.9 (m, 3 H); 9.3 (s, 1 H); 11.7 (s, 1 H); 13.3 (s, 1 H) |
| 172 | 1.4 (d, J = 6 Hz, 3 H); 2.4 (s, 3 H); 3.4 (s, 3 H); 3.9 (s, 3 H); 4.7 (q, 1 H); 6.5 (s, 1 H); 7.0–7.8 (m, 3 H); 9.2 (s, 1 H); 13.2 (s, 1 H) |
| 174 | 1.4 (d, J = 6 Hz, 3 H); 2.5 (s, 3 H); 3.9 (s, 3 H); 4.0 (s, 3 H); 5.2 (q, 1 H); 6.5 (s, 1 H); 7.1–7.9 (m, 3 H); 9.3 (bs, 1 H); 13.3 (bs, 1 H) |
| 175 | 1.0 (d, J = 7 Hz, 3 H); 2.3 (s, 3 H); 3.3 (s, 3 H); 3.5 (q, 1 H); 3.9 (s, 3 H); 6.5 (s, 1 H); 7.5–7.8 (m, 3 H); 10.6 (bs, 1 H); 13.7 (bs, 1 H) |
| 177 | d$_6$ acetone 1.4 (d, J = 6 Hz, 3 H); 2.5 (s, 3 H); 4.0 (s, 3 H); 4.6 (m, 2 H); 4.9 (q, J = 6 Hz, 1 H); 5.0–5.4 (m, 2 H); 5.7–6.2 (m, 1 H); 5.9 (s, 1 H); 7.0–7.9 (m, 3 H); 9.3 (s, 1 H); 13.3 (s, 1 H) |
| 178 | 1.0 and 1.2 (2 xd, total 3 H); 2.4 (s, 3 H); 3.4 (s, 3 H); 3.9 (s, 3 H); |

TABLE 2-continued

| Compound No. | Proton chemical Shift in ppm (d$_6$ DMSO) |
|---|---|
| | 4.1 (q, 1 H); 6.5 (s, 1 H); 7.7 (m, 3 H); 10.6 (bs, 1 H) 13.0 (bs, 1 H) |
| 181 | 1.26 (d, J = 7 Hz, 3 H); 2.37 (s, 3 H); 3.93 (s, 3 H); 4.74 (q, 1 H); 6.54 (s, 1 H); 7.1 (m, 2 H); 11.04 (bs, 1 H); other exchangeables not observed |
| 182 | 1.26 (d, J = 6 Hz, 3 H); 3.91 (s, 6 H); 4.77 (q, 1 H); 6.01 (s, 1 H); 7.1–7.8 (m, 2 H); 10.63 (s, 1 H); 11.1 (s, 1 H); 12.9 (s, 1 H) |
| 183 | 1.31 (d, J = 6 Hz, 3 H); 3.96 (s, 3 H); 4.81 (q, 1 H); 6.86 (s, 1 H); 7.1–7.8 (m, 2 H); 10.74 (s, 1 H), 11.1 (s, 1 H); 12.8 (s, 1 H) |
| 188 | Acetone 1.4 (s, 6 H); 2.5 (s, 3 H); 3.4 (s, 3 H); 4.0 (s, 3 H); 6.5 (s, 1 H); 7.1–7.8 (m, 3 H); 10.1 (s, 1 H); 13.2 (s, 1 H) |
| 192 | 1.27 (d, J = 6 Hz, 3 H); 3.30 (s, 3 H); 3.89 (s, 6 H); 4.80 (q, 1 H); 6.01 (s, 1 H); 7.37 (m, 2 H); 10.6 (bs, 1 H); 12.8 (bs, 1 H) |
| 193 | 1.31 (d, J = 6 Hz, 3 H); 2.36 (s, 3 H); 3.26 (s, 3 H); 3.90 (s, 3 H.); 4.80 (q, 1 H); 6.56 (s, 1 H); 7.1–7.7 (m, 2 H); 10.63 (s, 1 H); 13.40 (s, 1 H) |
| 200 | 1.28 (d, J = 6 Hz, 3 H); 3.88 (s, 6 H); 4.86 (q, 1 H); 6.0 (s, 1 H); 7.46 (d, 1 H); 7.56 (d, 1 H); |
| 201 | 1.0 (d, J = 7 Hz, 3 H); 2.3 (s, 3 H); 3.5 (q, 1 H) 3.9 (s, 3 H); 6.5 (s, 1 H); 7.3 (d, 1 H); 7.6 (d, 1 H); 10.7 (bs, 1 H); 11.0 (bs, 1 H); 12.8 (bs, 1 H) |
| 202 | 1.01 and 1.48 (2 d, J = 7 Hz, total 3 H); 2.43 (s, 3 H); 3.96 (s, 3 H); 4.19 (m, 1 H); 6.64 (s, 1 H); 7.34 (d, 1 H); 7.63 (d, 1 H); 11.11 (bs, 1 H); 11.15 (s, 1 H); 14.1 (bs, 1 H) |
| 204 | 1.28 (d, J = 6 Hz, 3 H); 3.32 (s, 3 H); 3.88 (s, 6 H); 4.86 (q, 1 H); 6.0 (s, 1 H); 7.46 (d, 1 H); 7.56 (d, 1 H); 10.5 (bs, 1 H); 12.8 (bs, 1 H) |
| 205 | 1.1 (d, J = 8 Hz, 3 H); 2.4 (s, 3 H); 3.4 (s, 3 H); 3.5 (q, 1 H); 3.9 (s, 3 H); 6.5 (s, 1 H); 7.6 (d, 1 H); 7.7 (d, 1 H); 10.6 (bs, 1 H); 14.0 (bs, 1 H) |
| 207 | 1.17 (d, J = 7 Hz, 3 H); 2.46 (s, 3 H); 3.60 (m, 1 H); 4.00 (s, 3 H); 6.57 (s, 1 H); 7.54 (s, 1 H); 7.89 (s, 1 H); 10.80 (s, 1 H); 11.1 (s, 1 H); 13.0 (bs, 1 H) |
| 208 | 1.22 (d, J = 7 Hz, 3 H); 2.37 (s, 3 H); 3.95 (s, 3 H); 6.34 (s, 1 H); 8.06 (s, 2 H); 11.0 (bs, 1 H) other exchangeables not observed |
| 226 | Not recorded. Immediate sulfonamide precursor spectrum: 2.57 (t, J = 7 Hz, 2 H); 3.54 (t, 2 H); 7.29 (bs, 2 H); 7.54 (s, 1 h); 8.09 (s, 1 H); 10.03 (s, 1 H) |
| 227 | Not recorded on sulfonyl urea. Immediate sulfonamide precursor spectrum: 2.60 (t, J = 7 Hz, 2 H); 3.14 (s, 3 H); 3.57 (t, J = 7 Hz, 2 H); 7.20 (s, 2 H); 7.54 (s, 1 H); 8.09 (s, 1 H) |
| 239 | 2.0 (bm, 2 H); 2.21 (s, 3 H); 2.37 (s, 3 H); 2.46 (s, 3 H); 2.8 (bm, 4 H); 4.36 (s, 2 H); 6.93 (s, 1 H); 10.3 (s, 1 H); 10.8 (s, 1 H); 13.1 (s, 1 H) |

Example 11

This non-limiting Example illustrates the preparation of formulations of the compounds of the invention.

(a) Emulsifiable Concentrate

Compound No. 36 was dissolved in toluene/DMSO containing 7% v/v "Teric" N13 and 3% v/v "Kemmat" SC15B to give an emulsifiable concentrate which was diluted with water to the required concentration to give an aqueous emulsion which was applied by spraying.

("Teric" is a Trade Mark and "Teric" N13, is a product of ethoxylation of nonylphenol; "Kemmat" is a Trade Mark and "Kemmat" SC15B is a formulation of calcium dodecylbenzenesulfonate.)

(b) Aqueous Suspension

Compound No. 36 (5 parts by weight) and "Dyapol" PT (1 part by weight) were added to a 2% aqueous solution (94 parts by weight) of "Teric" N8 and the mixture was ball milled to produce a stable aqueous suspension which may be diluted with water to the required concentration to give an aqueous suspension which may be applied by spraying.

("Dyapol" is a Trade Mark and "Dyapol" PT is an anionic suspending agent; "Teric" N8 is a product of ethoxylation of nonylphenol.)

(c) Emulsifiable Concentrate

Compound No. 36 (10 parts by weight), "Teric" N13 (5 parts by weight) and "Kemmat" SC15B (5 parts by weight) were dissolved in "Solvesso" 150 (80 parts by weight) to give an emulsifiable concentrate which may be diluted with water to the required concentration to give an aqueous emulsion which may be applied by spraying.

("Solvesso" is a Trade Mark and "Solvesso" 150 is a high boiling point aromatic petroleum fraction.)

(d) Dispersible Powder

Compound No. 1 (10 parts by weight), "Matexil" DA/AC (3 parts by weight), "Aerosol" OT/B (1 part by weight) and china clay 298 (86 parts by weight) were blended and then milled to give a powder composition having a particle size below 50 microns.

("Matexil" is a Trade Mark and "Matexil" DA/AC is the disodium salt of a naphthalenesulfonic acid/formaldehyde condensate; "Aerosol" is a Trade Mark and "Aerosol" OT/B is a formulation of the dioctyl ester of sodium sulfosuccinic acid.)

(e) Dusting Powder

Compound No. 1 (10 parts by weight), attapulgite (10 parts by weight) and pyrophyllite (80 parts by weight) were thoroughly blended and then ground in a hammermill to produce a powder of particle size less than 200 microns.

Emulsifiable concentrates and/or suspensions of the compounds of the invention were prepared essentially as described in part (a), (b) or (c) above and then diluted with water, optionally containing surface active agent and/or oil, to give aqueous compositions of the required concentration which were used, as described in Examples 12 and 13, in the evaluation of the pre-emergence and post-emergence herbicidal activity of the compounds.

Example 12

The pre-emergent herbicidal activity of the compounds of the invention formulated as described in Example 11 was assessed by the following procedure:

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glass house, lightly watered with an overhead spray to initiate germination and then sub-irrigated as required for optimum plant growth. After three weeks the boxes were removed from the glass house and the effect of the treatment was visually assessed. The results are presented in Table 3 where the damage to plants is rated on a scale from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiments was carried out.

The names of the test plants are as follows:

| | |
|---|---|
| Wh | Wheat |
| Ot | Wild Oats |
| Rg | Ryegrass |
| Jm | Japanese millet |
| B | Barley |
| P | Peas |
| Ip | Ipomea |
| Ms | Mustard |
| Sf | Sunflower | box of each of the monocotyledonous plants and the dicotyledonous plants was removed from the glass house and sprayed with the required quantity of a composition of the invention. After spraying the boxes were returned to the glass house for a further 3 weeks and the effect of treatment was visually assessed by comparison with the untreated controls. The results are presented in Table 4 where the damage to plants is rated on a scale from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (-) means that no experiment was carried out.

The names of the test plants are as follows:

| | |
|---|---|
| Wh | Wheat |
| Ot | Wild Oats |
| Rg | Ryegrass |
| Jm | Japanese millet |
| B | Barley |
| P | Peas |
| Ip | Ipomea |
| Ms | Mustard |
| Sf | Sunflower |

TABLE 3

Pre-emergent Herbicidal Activity

| Compound No | Application Rate Kg/ha | Wh | Jm | Rg | Ot | B | sf | Ip | Ms | P |
|---|---|---|---|---|---|---|---|---|---|---|
| 2 | 0.4 | 1 | 0 | 2 | 0 | 0 | 5 | 5 | 3 | 3 |
| 2 | 0.1 | — | — | — | — | — | 5 | 2 | 2 | 3 |
| 3 | 0.1 | 1 | 4 | 4 | 0 | 0 | 4 | — | — | 5 |
| 25 | 0.4 | 4 | 0 | 4 | 4 | 4 | 1 | 1 | 4 | 2 |
| 26 | 0.4 | 4 | 0 | 5 | 4 | 4 | 4 | 2 | 4 | 3 |
| 26 | 0.1 | — | — | — | — | — | 4 | 3 | 4 | 5 |
| 27 | 0.4 | 3 | 0 | 1 | 1 | 2 | 1 | 2 | 2 | 5 |
| 28 | 0.4 | 3 | 1 | 2 | 2 | 3 | 3 | 3 | 1 | 2 |
| 31 | 0.4 | 0 | — | 0 | 0 | 0 | 3 | 5 | 2 | 2 |
| 36 | 0.4 | 4 | 2 | 2 | 3 | 2 | 4 | 0 | 0 | 0 |
| 37 | 0.4 | 4 | 0 | 4 | 4 | 4 | 2 | 3 | 4 | 3 |
| 38 | 0.4 | 1 | 1 | 3 | 1 | 0 | 3 | 5 | 5 | 5 |
| 39 | 0.4 | 2 | 3 | 3 | 3 | 3 | 1 | 5 | 5 | 3 |
| 45 | 0.4 | 4 | 4 | 4 | 3 | 2 | 3 | 2 | 4 | 4 |
| 65 | 0.4 | 4 | 2 | 3 | 2 | 0 | 4 | 5 | 0 | 1 |
| 113 | 0.4 | 0 | 0 | 0 | 0 | 0 | 2 | 5 | 4 | 1 |
| 115 | | | | | | | | | | |
| 150 | 0.4 | 4 | 2 | 4 | 2 | 3 | 3 | 3 | 4 | 5 |
| 150 | 0.1 | — | — | — | — | — | 2 | 3 | 3 | 5 |
| 151 | 0.4 | 4 | 4 | 4 | 3 | 3 | 3 | 2 | 3 | 4 |
| 169 | 0.4 | 4 | 3 | 3 | 3 | 3 | 3 | 2 | 3 | 5 |
| 172 | 0.4 | 4 | 2 | 4 | 3 | 3 | 1 | 1 | 3 | 4 |
| 174 | 0.4 | 3 | 2 | 2 | 2 | 3 | 0 | 2 | 2 | 2 |
| 182 | 0.4 | 4 | 4 | 4 | 3 | 3 | 3 | 2 | 3 | 2 |
| 193 | 0.4 | 4 | 0 | 3 | 3 | 3 | 1 | 1 | 2 | 1 |
| 204 | 0.4 | 2 | 2 | 2 | 2 | 3 | 1 | 1 | 1 | 0 |

Example 13

The post-emergent herbicidal activity of the compounds of the invention formulated as described in Example 11 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glass house, lightly watered with an overhead spray to initiate germination and then sub-irrigated as required for optimum plant growth. After the plants had grown to a height of about 10 to 12.5 cm one

TABLE 4

Post-emergent Herbicidal Activity

| Compound No | Application Rate Kg/ha | Wh | Jm | Rg | Ot | B | sf | Ip | Ms | P |
|---|---|---|---|---|---|---|---|---|---|---|
| 1 | 0.4 | 2 | 1 | 1 | 3 | 3 | 1 | 2 | 5 | 3 |
| 2 | 0.4 | 3 | 4 | 4 | 3 | 4 | 4 | 5 | 5 | 4 |
| 2 | 0.1 | — | — | — | — | — | 4 | 4 | 5 | 4 |
| 2 | 0.025 | — | — | — | — | — | 3 | 3 | 5 | 3 |
| 3 | 0.4 | 3 | — | 4 | 3 | 3 | 4 | 3 | 4 | 3 |
| 3 | 0.1 | 0 | 0 | 0 | 0 | 1 | 4 | 1 | 4 | 2 |
| 3 | 0.025 | — | — | — | — | — | 2 | 0 | 2 | 2 |
| 28 | 0.4 | 1 | 0 | 1 | 1 | 1 | 4 | 1 | 1 | 3 |
| 31 | 0.4 | 3 | 2 | 2 | 3 | 2 | 4 | 3 | 4 | 3 |
| 31 | 0.1 | — | — | — | — | — | 4 | 3 | 4 | 2 |
| 32 | 0.4 | 2 | 2 | 3 | 4 | 3 | 4 | 2 | 3 | 3 |
| 36 | 0.4 | 4 | 0 | 3 | 4 | 4 | 5 | — | 3 | 4 |
| 37 | 0.4 | 4 | 0 | 3 | 5 | 4 | 5 | 3 | 4 | 3 |
| 46 | 0.4 | 4 | 4 | 3 | 4 | 4 | 3 | 5 | 4 | 4 |
| 46 | 0.1 | — | — | — | — | — | 3 | 4 | 3 | 3 |
| 57 | 0.4 | 3 | 3 | 0 | 3 | 4 | 0 | 4 | 2 | 3 |
| 65 | 0.4 | 4 | 1 | 5 | 5 | 4 | 5 | — | 5 | 5 |
| 65 | 0.1 | — | — | — | — | — | 5 | 4 | 5 | 3 |
| 66 | 0.4 | 4 | 1 | 3 | 4 | 3 | 5 | — | 5 | 5 |
| 66 | 0.1 | — | — | — | — | — | 5 | 0 | 4 | 4 |
| 80 | 0.4 | 3 | 0 | 0 | 3 | 2 | 3 | 0 | 1 | 3 |
| 84 | 0.4 | 3 | — | 3 | 3 | 2 | 2 | 1 | 3 | 2 |
| 98 | 0.4 | 0 | — | 3 | 0 | 2 | 2 | 0 | 1 | 2 |
| 150 | 0.4 | 1 | 1 | 0 | 2 | 2 | 4 | 3 | 2 | 1 |
| 151 | 0.4 | 3 | 2 | 2 | 2 | 2 | 4 | 3 | 2 | 2 |
| 169 | 0.4 | 2 | 2 | 2 | 2 | 2 | 4 | 2 | 2 | 3 |
| 172 | 0.4 | 2 | 2 | 1 | 3 | 2 | 3 | 2 | 1 | 1 |
| 174 | 0.4 | 2 | 2 | 2 | 3 | 2 | 3 | 2 | 2 | 2 |
| 193 | 0.4 | 3 | 2 | 3 | 3 | 3 | 4 | 3 | 3 | 2 |
| 201 | 0.4 | 2 | 0 | 0 | 4 | 3 | 4 | 0 | 4 | 3 |
| 202 | 0.4 | 1 | 0 | 0 | 0 | 1 | 2 | 3 | 0 | 1 |
| 204 | 0.4 | 3 | 0 | 1 | 3 | 2 | 3 | 5 | 2 | 2 |
| 205 | 0.4 | 3 | 3 | 1 | 3 | 3 | 3 | — | 2 | 3 |
| 208 | 0.4 | 0 | 0 | 0 | 0 | 1 | 3 | 2 | 2 | 1 |

Example 14

The compounds were formulated for test by mixing an appropriate amount with 5 ml of an emulsion prepared by diluting 160 ml of a solution containing 21.9 g per liter of "Span" 80 and 78.2 g per liter of "Tween" 20 in methylcyclohexanone to 500 ml with water. "Span"

80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 5 below. Damage to test plants was assessed after 14 days on a scale of 0 to 5 wherein 0 is 0 to 20% damage and 5 is complete kill.

The degree of herbicidal damage was assessed by comparision with untreated control plants. The results are given in Table 5 below. A dash (-) means no experiment was carried out.

The names of the test plants were as follows:

| | |
|---|---|
| Sb | Sugar Beet |
| Rp | Oilseed Rape |
| Ct | Cotton |

-continued

| | |
|---|---|
| Sy | Soya Bean |
| Mz | Maize |
| Ww | Winter wheat |
| Rc | Rice |
| Bd | *Bidens pilosa* |
| Ip | Ipomea |
| Am | *Amaranthus retroflexus* |
| Pi | Polygonum |
| Ca | *Chenopodium album* |
| Ga | *Galium aparine* |
| Xs | *Xanthium spinosum* |
| Ab | *Abutilon theophrasti* |
| Co | *Cassia obtusifolia* |
| Av | *Avena fatua* |
| Dg | *Digitaria sanguinalis* |
| Al | *Alopecurus myosuroides* |
| St | *Setaria viridis* |
| Ec | *Echinochloa crus-galli* |
| Sh | *Sorghum halepense* |
| Ag | *Agropyron repens* |
| Cn | *Cyperus rotundus* |

TABLE 5

Post-Emergent Herbicidal Activity

| Test Plants | Compound No. 2 | 2 | 3 | 3 | 25 | 26 | 27 | 28 | 38 | 41 | 45 | 78 | 140 | 151 |
|---|---|---|---|---|---|---|---|---|---|---|---|---|---|---|
| Rate g/ha | 125 | 25 | 25 | 5 | 25 | 25 | 125 | 125 | 25 | 125 | 25 | 125 | 125 | 18 |
| Sb | 4 | 3 | 4 | 3 | 4 | 4 | 4 | 3 | 1 | — | 2 | 0 | 2 | 2 |
| Rp | 5 | 5 | 4 | 3 | 4 | 4 | 4 | 4 | 4 | — | 3 | 4 | 1 | 4 |
| Ct | 1 | 1 | 3 | 2 | 3 | 3 | 0 | 1 | 1 | — | 2 | 0 | 1 | 3 |
| Sy | 3 | 3 | 3 | 3 | 3 | 3 | 2 | 2 | 3 | — | 4 | 3 | 2 | 3 |
| Mz | 4 | 4 | 3 | 3 | 3 | 3 | 3 | 3 | 2 | — | 3 | 3 | 2 | 3 |
| Ww | 3 | 3 | 3 | 2 | 3 | 3 | 4 | 4 | 3 | — | 3 | 2 | 4 | 3 |
| Rc | 3 | 3 | 3 | 1 | 2 | 2 | 1 | 2 | 1 | — | 2 | 0 | 0 | 2 |
| Bd | 4 | 4 | 3 | 3 | 3 | 4 | 1 | 4 | 3 | — | 3 | 4 | 1 | 4 |
| Ip | 4 | 1 | 1 | 0 | 2 | 2 | 1 | 1 | 2 | 2 | 3 | 0 | 0 | 3 |
| Am | 4 | 3 | 5 | 3 | 4 | 4 | 4 | 5 | 3 | — | 3 | 3 | 1 | 3 |
| Pi | 1 | 1 | 4 | 1 | 1 | 3 | 1 | 3 | 1 | 0 | 3 | 2 | 0 | 2 |
| Ca | 4 | 4 | 3 | 1 | 3 | 3 | 3 | 2 | 2 | 1 | 3 | 2 | 0 | 2 |
| Ga | — | — | 4 | 3 | 3 | 4 | 3 | 3 | 3 | 2 | 3 | 2 | 0 | 4 |
| Xs | 4 | 3 | 4 | 2 | 2 | 1 | 2 | 2 | 2 | 1 | 2 | 4 | 0 | 4 |
| Ab | 4 | 3 | 3 | 2 | 3 | 3 | 2 | 3 | 3 | 2 | 3 | 2 | 0 | 3 |
| Co | 3 | 3 | 3 | 2 | 2 | 4 | 3 | 2 | 3 | 0 | 2 | 2 | 2 | 3 |
| Av | 4 | 3 | 3 | 2 | 4 | 3 | 3 | 4 | 4 | 3 | 3 | 3 | 1 | 4 |
| Dg | 3 | 3 | 3 | 1 | 2 | 1 | 1 | 1 | 2 | — | 3 | 2 | 1 | 3 |
| Al | 4 | 4 | 3 | 2 | 4 | 3 | 4 | 4 | 3 | 1 | 3 | 1 | 3 | 3 |
| St | 4 | 3 | 4 | 2 | 3 | 3 | 1 | 3 | 1 | 2 | 2 | 0 | 1 | 3 |
| Ec | 4 | 4 | 3 | 1 | 3 | 1 | 3 | 2 | 3 | — | 4 | 3 | 0 | 4 |
| Sh | 4 | 4 | 3 | 3 | 4 | 4 | 3 | 4 | 3 | 4 | 3 | 3 | 1 | 4 |
| Ag | 3 | 2 | 2 | 2 | 2 | 3 | 3 | 4 | 2 | — | 3 | 1 | 1 | 3 |
| Cn | 3 | 2 | 3 | 3 | 2 | 2 | 1 | 2 | 1 | 0 | 2 | 1 | 1 | 2 |

| Test Plants | Compound No. 169 | 169 | 174 | 181 | 182 | 182 | 192 | 192 | 204 | 200 |
|---|---|---|---|---|---|---|---|---|---|---|
| Rate g/ha | 125 | 25 | 125 | 25 | 25 | 5 | 125 | 500 | 125 | 125 |
| Sb | 3 | 3 | 3 | 4 | 1 | 0 | 0 | 0 | 1 | 0 |
| Rp | 4 | 3 | 3 | 4 | 4 | 2 | 4 | 3 | 4 | 3 |
| Ct | 3 | 2 | 2 | 3 | 3 | 1 | 1 | 1 | 1 | 1 |
| Sy | 3 | 3 | 2 | 2 | 3 | 1 | 3 | 2 | 3 | 3 |
| Mz | 3 | 3 | 3 | 2 | 2 | 3 | 3 | 2 | 3 | 3 |
| Ww | 4 | 3 | 3 | 3 | 3 | 3 | 3 | 2 | 3 | 3 |
| Rc | 3 | 3 | 2 | 0 | 2 | 2 | 2 | 1 | 2 | 2 |
| Bd | 4 | 4 | 4 | 3 | 3 | 2 | 3 | 2 | 3 | 3 |
| Ip | 3 | 3 | 3 | 3 | 2 | 2 | 3 | 2 | 2 | 3 |
| Am | 4 | 3 | 3 | 3 | 4 | 2 | 4 | 3 | 3 | 4 |
| Pi | 3 | 2 | 3 | 2 | 3 | 2 | 3 | 3 | 3 | 3 |
| Ca | 3 | 2 | 3 | 3 | 1 | 0 | 2 | 1 | 2 | 2 |
| Ga | 4 | 3 | 3 | 3 | 3 | 2 | 3 | 3 | 3 | 3 |
| Xs | 4 | 4 | 2 | 2 | 3 | 1 | 3 | 2 | 2 | 3 |
| Ab | 4 | 3 | 2 | 3 | 3 | 1 | 2 | 2 | 1 | 3 |
| Co | 3 | 2 | 2 | 2 | 2 | 1 | 3 | 1 | 1 | 2 |
| Av | 4 | 2 | 3 | 3 | 4 | 3 | 3 | 4 | 3 | 3 |
| Dg | 4 | 3 | 3 | 2 | 2 | 2 | 2 | 3 | 1 | 1 |
| Al | 4 | 3 | 3 | 3 | 4 | 3 | 3 | 4 | 3 | 3 |
| St | 3 | 2 | 2 | 1 | 2 | 1 | 3 | 3 | 3 | 1 |
| Ec | 3 | 3 | 3 | 3 | 4 | 2 | 4 | 3 | 4 | 3 |

TABLE 5-continued

| | Post-Emergent Herbicidal Activity | | | | | | | | | |
|---|---|---|---|---|---|---|---|---|---|---|
| Sh | 4 | 3 | 3 | 2 | 3 | 2 | 3 | 2 | 4 | 3 |
| Ag | 3 | 3 | 3 | 2 | 3 | 3 | 3 | 2 | 3 | 3 |
| Cn | 3 | 2 | 2 | 0 | 3 | 0 | 3 | 2 | 1 | 3 |

We claim:

1. A compound of formula I and the salts thereof

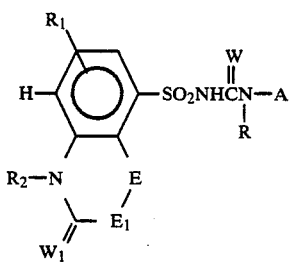

wherein

W and $W_1$ are independently O or S;

E is O, $S(O)_m$ or $N-R_3$;

$E_1$ is $CH_2$, $CH_2CH_2$, $CH(C_1-C_4$ alkyl), $C(CH_3)_2$ or CH aryl; $R_1$ is hydrogen, halogen, $C_1-C_4$ alkyl, $C_1-C_4$ haloalkyl, $C_1-C_4$ alkoxy, $C_1-C_4$ halo-alkoxy, $C_1-C_4$ alkoxycarbonyl, $C_1-C_4$ alkylthio, $C_1-C_4$ alkylsulfinyl, $C_1-C_4$ alkylsulfonyl, sulfamoyl, $C_1-C_4$ alkylsulfamoyl, di($C_1-C_4$ alkyl)sulfamoyl, amino, $C_1-C_4$ alkylamino, or di($C_1-C_4$ alkyl)amino;

R, $R_2$ and $R_3$ are independently hydrogen, $C_1-C_4$ alkyl, $C_2-C_4$ alkenyl or $C_2-C_4$ alkynyl; m=0, 1 or 2;

X is $CH_3$, $OCH_3$, $OCH_2CH_3$, Cl, F, Br, I, $OCF_2H$, $CH_2F$ or $CF_3$, Y is H, $CH_3$, $OCH_3$, $OC_2H_5$, $CH_2OCH_3$, $NH_2$, $NHCH_3$, $N(CH_3)_2$, $C_2H_5$, $CF_3$, $SCH_3$, $N(OCH_3)CH_3$, $OCH_2CH\text{-}CH_2$, $OCH_2C\text{-}CH$, $OCH_2CF_3$, cyclopropyl, Q $OCH_2CH_2OCH_3$, $CH_2SCH_3$, (C=O)$R_4$, $CR_4(QCH_3)_2$,

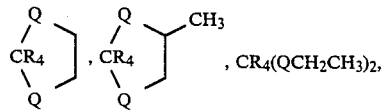, $CR_4(QCH_2CH_3)_2$, $OCF_2H$, $SCF_2H$, C≡CH or C≡CCH$_3$ where Q is O or S and $R_4$ is H or $CH_3$; and Z is CH, CCH$_3$, CC$_2$H$_5$, CCl or CBr.

2. A compound according to claim 1, wherein E, is selected from $CH_2$, $CH_2CH_2$, $CH(C_1-C_4$ alkyl) or $C(CH_3)_2$.

3. A compound according to claim 1, wherein W is O.

4. A compound according to claim 1, wherein
R is hydrogen;
$R_1$ is hydrogen, fluorine, chlorine, bromine, methyl, methoxy, trifluoromethyl or methylthio; and
Y is methyl, methoxy, ethoxy, methoxymethyl, trifluoromethyl, 2,2,2-trifluoroethoxy, dimethoxymethyl or difluoromethoxy.

5. A compound according to claim 1, wherein:
E is O, S, NH or NCH$_3$;
$E_1$ is $CH_2$, $CH_2CH_2$, or $CH(CH_3)$;
$W_1$ is O, and $R_2$ is hydrogen, methyl or ethyl.

6. A herbicidal composition comprising an effective amount of a compound according to claim 1 and a carrier therefor.

7. A process for severely damaging or killing unwanted plants which process comprises applying to the plants, or to the growth medium of the plants, an effective amount of a compound according to claim 1.

8. A process for controlling weeds in cultivated crops which process comprises applying to the crop, or to the growth medium of the crop, a compound according to claim 1 in an amount sufficient to severely damage or kill the weeds but insufficient to damage the crop substantially.

9. A process for regulating the growth of a plant which process comprises applying to the plant, to the seed of the plant, or to the growth medium of the plant, an effective amount of a compound according to claim 1.

10. A plant growth regulating composition comprising a compound according to claim 1 and an inert carrier therefor.

* * * * *

UNITED STATES PATENT AND TRADEMARK OFFICE
CERTIFICATE OF CORRECTION

PATENT NO. : 4,929,269

DATED : May 29, 1990

INVENTOR(S) : WATSON ET AL

It is certified that error appears in the above-identified patent and that said Letters Patent is hereby corrected as shown below:

Col. 35, between lines 34 and 35, insert the following formula:

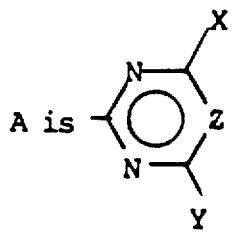

A-1

Signed and Sealed this

Twentieth Day of August, 1991

*Attest:*

HARRY F. MANBECK, JR.

*Attesting Officer*     *Commissioner of Patents and Trademarks*